United States Patent
Soerens et al.

(10) Patent No.: US 6,822,135 B2
(45) Date of Patent: Nov. 23, 2004

(54) FLUID STORAGE MATERIAL INCLUDING PARTICLES SECURED WITH A CROSSLINKABLE BINDER COMPOSITION AND METHOD OF MAKING SAME

(75) Inventors: Dave Allen Soerens, Neenah, WI (US); Lawrence Howell Sawyer, Neenah, WI (US); Kambiz Bayat Makoui, Neenah, WI (US); Jian Qin, Appleton, WI (US); Jason Matthew Laumer, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 111 days.

(21) Appl. No.: 10/206,888

(22) Filed: Jul. 26, 2002

(65) Prior Publication Data

US 2004/0024092 A1 Feb. 5, 2004

(51) Int. Cl.$^7$ ................................................ A61F 13/16
(52) U.S. Cl. ..................... 604/366; 604/365; 524/733; 524/837; 442/118; 442/119; 428/326; 428/331; 428/323
(58) Field of Search ................................ 524/837, 733, 524/13; 428/326, 331, 323; 442/118, 119; 604/366, 365

(56) References Cited

U.S. PATENT DOCUMENTS

| | | |
|---|---|---|
| 3,617,362 A | 11/1971 | Bemmels et al. |
| 3,944,702 A * | 3/1976 | Clark ........................ 442/327 |
| 3,951,893 A | 4/1976 | Gander |
| 3,963,605 A | 6/1976 | Seabourn |
| 4,251,643 A | 2/1981 | Harada et al. |
| 4,291,136 A | 9/1981 | Keogh |
| 4,328,323 A | 5/1982 | Keogh |
| 4,343,917 A | 8/1982 | Keogh |
| 4,353,997 A | 10/1982 | Keogh |
| 4,369,289 A | 1/1983 | Keogh |
| 4,408,011 A | 10/1983 | Barnabeo |
| 4,434,272 A | 2/1984 | Keogh |
| 4,440,907 A | 4/1984 | Keogh |
| 4,446,279 A | 5/1984 | Keogh |
| 4,459,396 A | 7/1984 | Yamasaki et al. |
| 4,489,029 A | 12/1984 | Keogh et al. |
| 4,493,924 A | 1/1985 | Rifi |
| 4,526,930 A | 7/1985 | Keogh |
| 4,551,504 A | 11/1985 | Barnabeo |
| 4,575,535 A | 3/1986 | Keogh |
| 4,579,913 A | 4/1986 | Keogh |
| 4,593,071 A | 6/1986 | Keogh |
| 4,676,820 A | 6/1987 | Le Sergent et al. |
| 4,753,993 A | 6/1988 | Keogh |
| 4,921,136 A | 5/1990 | Roggenburg, Jr. |
| 4,940,646 A | 7/1990 | Pawlowski |
| 5,047,476 A | 9/1991 | Keogh |
| 5,089,564 A | 2/1992 | Bullen |
| 5,112,919 A | 5/1992 | Furrer et al. |
| 5,145,906 A | 9/1992 | Chambers et al. |
| 5,196,470 A | 3/1993 | Anderson et al. |
| 5,204,404 A | 4/1993 | Werner, Jr. et al. |
| 5,252,660 A * | 10/1993 | Hazan et al. ............... 524/504 |
| 5,364,382 A | 11/1994 | Latimer et al. |
| 5,389,728 A | 2/1995 | Prejean |
| 5,498,478 A * | 3/1996 | Hansen et al. .............. 428/372 |
| 5,532,350 A | 7/1996 | Cottrell et al. |
| 5,656,132 A | 8/1997 | Farrington, Jr. et al. |
| 5,853,867 A | 12/1998 | Harada et al. |
| 5,859,074 A * | 1/1999 | Rezai et al. .................. 521/54 |
| 5,932,668 A | 8/1999 | Friebe et al. |
| 5,961,763 A * | 10/1999 | Makoui et al. ............. 156/204 |
| 6,020,071 A | 2/2000 | Watson |
| 6,054,523 A | 4/2000 | Braun et al. |
| 6,300,275 B1 | 10/2001 | Weir |
| 6,380,298 B2 | 4/2002 | Flautt et al. |
| 6,403,857 B1 * | 6/2002 | Gross et al. ................ 604/365 |
| 6,417,425 B1 | 7/2002 | Whitmore et al. |
| 6,596,103 B1 * | 7/2003 | Hansen et al. ............. 156/62.2 |
| 6,596,402 B2 | 7/2003 | Soerens et al. |
| 6,689,934 B2 | 2/2004 | Dodge, II et al. |
| 2003/0149413 A1 | 8/2003 | Mehawej |

FOREIGN PATENT DOCUMENTS

| | | |
|---|---|---|
| CA | 756190 | 4/1967 |
| EP | 1 013 291 A1 | 6/2000 |
| EP | 0 992 252 | 12/2000 |
| EP | 1 199 059 A1 | 4/2002 |
| WO | 99/57201 | 11/1999 |

* cited by examiner

Primary Examiner—Margaret G. Moore
(74) Attorney, Agent, or Firm—Pauley Petersen & Erickson

(57) ABSTRACT

A fluid storage material including particles, such as superabsorbent particles and/or microencapsulated fragrance agents, cleansing agents, or skin rejuvenation agents, secured to one another and/or secured to a substrate. The fluid storage material can be made by dispersing particles in a crosslinkable binder solution, applying the combined particles and binder solution to a surface such as a substrate or a release surface, inducing crosslinking of the binder, and removing the solvent from the surface such as, for example, by drying the solvent. The fluid storage material is particularly suitable for use in personal care products.

68 Claims, 7 Drawing Sheets

FLUID STORAGE MATERIAL INCLUDING PARTICLES SECURED WITH A CROSSLINKABLE BINDER COMPOSITION AND METHOD OF MAKING SAME

BACKGROUND OF THE INVENTION

This invention is directed to a fluid storage material, and a method of making a fluid storage material, in which particles are secured to one another and/or to a substrate with a crosslinkable binder composition.

Personal care absorbent products typically include an absorbent layer or an absorbent assembly to absorb and retain liquids, and a number of non-absorbent structural layers and non-absorbent structural components to maintain the absorbent layer in a desired location or to enhance the functionality of the absorbent layer. Each component in the absorbent product serves a specific purpose. As more features and functions are added to the product, the bulk of the product tends to increase.

An absorbent layer with a high absorbent capacity is typically bulkier than an absorbent layer with a lower absorbent capacity. For purposes of discretion and comfort, it is desirable to have as thin an absorbent layer as possible, without sacrificing absorbent capacity. Superabsorbent materials make it possible for absorbent layers to be thin while maintaining a high absorbent capacity, but even garments containing absorbent layers of superabsorbent material may be relatively bulky due to all of the additional features of the garment included to prevent leakage, such as surge layers and additional absorbent material in target areas.

Containment flaps are often included around leg openings to capture any excess fluid around the leg openings, while waist dams may be included around the waist opening to prevent the escape of any excess fluid through the waist opening. Although these additional components may be somewhat absorbent, these components typically do not contain the high absorbency of superabsorbent particles (SAP) because of the difficulty in keeping superabsorbent particles attached to a substrate, particularly in a swollen or wet condition.

Various techniques are known for creating additional absorbency in personal care absorbent articles. For example, it is known to use alkoxysilane-grafted poly(ethylene oxide) as an absorbent coating, thereby creating absorbency on non-absorbent surfaces. However, the resulting absorbent surfaces have less absorbent capacity than SAP.

As another example, it is known to produce an absorbent material by applying a water-softened superabsorbent to a supporting substrate without any additional adhesives. However, use of water alone does not provide for attachment in the wet condition.

As yet another example, it is known to react SAP with a polyhydroxy organic compound, such as glycerol, to form covalent bonds with the SAP. These covalent bonds attach the particles to each other and to a suitable substrate. Formation of covalent bonds with the SAP is expected to create stresses during the swelling process that would either inhibit swelling of the SAP or rupture the membrane coating.

Also, it is known to create individual superabsorbent fibers having high absorbent capacity. Such fibers can be formed by combining a superabsorbent resin with a binder component and adding the combination to a fiber base material in a non-bonded web form. The individual fibers have considerable absorbent capacity.

Furthermore, it is known to create absorbent composites containing fine, hydratable microfibril fibers obtained from cellulose or derivatives capable of swelling in water. These fibers can be used to coat superabsorbent particles. The microfibrilar cellulose fiber coating provides a measure of binding to a supporting sheet, such as a nonwoven fabric. Since the microfibrilar cellulose fibers coat the superabsorbent particles, the fibers tend to inhibit migration of the superabsorbent particles but do not form durable attachments, especially when wet. Conventional adhesive materials used to increase or enhance durability of attachment tend to limit access of liquids to the superabsorbent or create significant constraining forces that limit superabsorbent swelling and therefore ultimate capacity.

U.S. Pat. No. 6,403,857 to Gross et al. describes an absorbent structure including an integral layer of superabsorbent polymer particles. The water-swellable superabsorbent polymer particles are adhered to an absorbent layer using a water-based polymeric binder that is latex bonded and/or thermally bonded. Gross et al. also describe a binder that may be a carboxylic polyelectrolyte in admixture with a crosslinking agent. The crosslinking agent has the property of reacting with carboxylic or carboxylate groups of the polyelectrolyte.

Other recent development efforts have provided coating materials for a variety of uses. For example, U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Others have reported the production of graft copolymers having silane functional groups that permitted the initiation of cross-linking by exposure to moisture. Prejean (U.S. Pat. No. 5,389,728) describes a melt-processible, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings.

Furrer et al., in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136. Since the cured products of these formulations are reported to be useful for coverings for wire and cable, and for non-conductive coatings for electrical conductors, it would be expected that they are durable coatings for which properties such as water absorbency and biodegradability would be a disadvantage.

Water-swellable polymers have reportedly been produced by cross-linking water soluble polymers, such as poly (ethylene oxide). It is known that poly(alkylene oxides), such as poly(ethylene oxide), can be cross-linked through gamma irradiation. Depending upon the degree of irradiation and the degree of cross-linking, the properties of the cross-linked polymer can range from a water soluble material to a hard solid with no appreciable water absorbency. Materials that are substantially non-water soluble, but still absorbent can be made. However, the use of gamma rays requires expensive equipment and time consuming procedures due to safety concerns, and the degree of cross-linking that is obtained is often difficult to control.

Several references have reported the use of chemical cross-linking groups as a method of avoiding the dangers and costs associated with the use of ionizing radiation. U.S. Pat. No. 3,963,605 to Chu reported a water-swellable, cross-linked poly(alkylene oxide) that was produced by heating a mixture of poly(ethylene oxide) with acrylic acid and a free radical initiator such as acetyl peroxide in a hydrocarbon solvent such as hexane, heptane, or cyclohexane. Another alternative was reported in Canadian Pat. No. 756,190, and involved cross-linking through a di-vinyl monomer in the presence of a free radical catalyst. The use of other cross-linking agents, such as a diacrylate, or methyl-bis-acrylamide with a free radical inhibitor, have also been reported.

Lubricious coatings of cross-linked, hydrophilic polyurethane have been reported by Watson in U.S. Pat. No. 6,020,071. Another polyurethane coating is described by Tedeshchl et al., in EP 0992 252 A2, where a lubricious, drug-accommodating coating is described that is the product of a polyisocyanate; an amine donor; and/or a hydroxyl donor; and an isocyanatosilane adduct having terminal isocyanate groups and an alkoxy silane. A water soluble polymer, such as poly(ethylene oxide), can optionally be present. Cross-linking causes a polyurethane or a polyurea network to form, depending upon whether the isocyanate reacts with the hydroxyl donors or the amine donors. This composition provides lubricious benefits from a particular chemistry, which does not appear to provide high absorbency.

There is a need or desire for a fluid storage material that is thin, durable, and possesses a high absorbent capacity. There is a further need or desire for a method of attaching particles to a substrate such that the particles will remain attached to the substrate even while in a swollen or wet condition without causing a significant decrease in absorbent capacity.

SUMMARY OF THE INVENTION

In response to the discussed difficulties and problems encountered in the prior art, a new fluid storage material that provides additional utility to the non-absorbent structural components of personal care absorbent products as carriers of absorbent capacity has been discovered. This capability provides for thinner, more conformable products having greater absorbent capacity. Furthermore, the fluid storage material may provide additional functionality such as odor control, cleansing properties, and skin rejuvenation properties, for example.

The fluid storage material includes particles secured to one another and/or secured to a substrate by a crosslinkable binder composition. Use of the crosslinkable binder provides enhanced attachment of the particles in a swollen or wet condition. Furthermore, the binder does not reduce the effective absorbent capacity of the particles and may contribute an additional absorbent capacity of its own.

The crosslinkable binder composition includes a crosslinkable binder that is sufficiently hydrophilic to provide uninhibited access of aqueous fluids to the particles. The crosslinkable binder may be a soluble binder made up of hydrophilic polymers, a blend of hydrophilic polymers containing hydrophilic agents, and/or a blend of hydrophobic polymers containing hydrophilic agents. For example, the binder may be an alkoxysilane-grafted poly(ethylene oxide). One suitable alkoxysilane is methacryloxypropyl trimethoxy silane. As another example, the binder composition may include acrylic acid copolymers and long chain, hydrophilic acrylate or methacrylate esters, such as poly (ethylene glycol) methacrylate having from 1 to 12 ethylene glycol units. Crosslinking capability is provided by acrylate or methacrylate esters that have a functional group that is capable, upon exposure to water, of forming a silanol functional group that condenses to form a crosslinked polymer. A suitable example of such a methacrylate ester is methacryloxypropyl trimethoxy silane.

The binder in the crosslinkable binder composition suitably has a glass transition temperature below about 30 degrees Celsius, or below about 10 degrees Celsius. The crosslinkable binder composition desirably has a bending modulus lower than the bending modulus of the substrate.

In addition to the crosslinkable binder, the crosslinkable binder composition may also include a solvent that does not substantially swell or adversely affect the particles. Suitably, the solvent provides solubility of the binder, and less than 10% by weight of the solvent is imbibed by the particles. An example of a suitable solvent includes alcohol, such as between about 99.5% and about 50% alcohol by weight, and between about 0.5% and about 50% water by weight. In addition to the binder and the solvent, the binder composition may also include one or more modifying agents, such as plasticizers, colorants, and preservatives.

Alternatively, the binder composition may be heated in a suitable device, such as an extruder, to a flowable condition followed by addition of suitable particles to provide a flowable mixture of binder and particles. The particles may be superabsorbent particles, including, for example, a crosslinked form of sodium polyacrylate, sodium polymethacrylate, polyacrylamide, carboxymethyl cellulose, grafted starch, poly(sodium aspartate), poly(vinyl amine), poly(dimethyldiallyl amine), chitosan salt, and/or poly(ethylene imine). Suitably, the particles have a diameter of between about 50 and about 800 microns, or between about 200 and about 400 microns. For some printing applications, the particles may have a diameter of between about 60 and about 80 microns. The particles and the binder may be present in a ratio of between about 1:4 and about 20:1 on the substrate.

Alternatively, or in addition to the superabsorbent, the particles may include an encapsulated agent. For example, the particles may include encapsulated fragrance agents, cleansing agents, and/or skin rejuvenation agents. As another alternative, the particles may be in a powder form, such as activated carbon or sodium bicarbonate.

The substrate may be a nonwoven web, a woven web, a knitted fabric, a sheet of cellulose tissue, a plastic film, a stranded composite, an elastomer net composite, or any other suitable substrate. Examples of suitable types of plastic film substrates include those made of polypropylene, low density polyethylene, high density polyethylene, linear low density polyethylene, and ultra low density polyethylene.

Alternatively, the substrate may be a release surface. Application of the binder/particle mixture provides, after removal of solvent or cooling of a solvent-free flowable mass, a cohesive film or network composed of particles adhered to each other by the binder composition. The resulting thin, high density, flexible film or network of particles can provide the fluid retention function of an absorbent product.

As a further embodiment, the fluid storage material may include the crosslinkable, absorbent, film-forming binder; particles; and fibers. Suitable fibers include, but are not limited to, cellulose powder which is obtained by grinding birch (or other) hardwood fiber to a smaller particle size powder. Other suitable fibers include other hardwood fibers, both northern and southern, including mercerized southern hardwood fibers, and chemically stiffened southern softwood pulp, as well as superabsorbent fibers.

As mentioned, the fluid storage material can be used to make personal care absorbent articles, thereby providing absorbent capacity to non-absorbent structural layers that typically provide little or no absorbent capacity. These modified structural layers suitably have a thickness of between about 0.2 and about 4 millimeters (mm), when measured at a pressure of 0.05 psi, and an absorbent capacity of between about 0.1 and about 1.8 grams per square centimeter ($g/cm^2$). Examples of articles in which the fluid storage material may be used include diapers, diaper pants, training pants, feminine hygiene products, incontinence products, swimwear garments, and the like.

The fluid storage material of the invention can be made by dispersing particles in the crosslinkable binder solution described above, and applying the particles in solution to a substrate or to a release surface. The combined particles in solution may be applied to the substrate or release surface, either continuously or in a pattern, using any of a variety of application processes, including knife over roll coating, roll coating, spraying, and printing. Examples of suitable printing processes include gravure printing, silk screen, and ink jet printing. After the particles in solution have been applied to the substrate or release surface, crosslinking of the binder is then induced. Crosslinking may be induced by a variety of techniques including thermal initiation, radiation initiation, redox chemical reactions, multivalent metal ions, and moisture. Various types of effective radiation initiation include ultraviolet, microwave, and electron-beam radiation. Moisture initiation may be accomplished through hydrolysis and condensation. Multivalent metal ions can initiate crosslinking by complexation. After inducing crosslinking of the binder, the solvent can be removed from the substrate, either by drying the substrate or using any other effective technique to evaporate the solvent.

Alternatively, the binder composition may be heated in a suitable device, such as an extruder, to a flowable condition followed by addition of the particles to provide a substantially solvent-free, flowable mixture of binder and particles. Upon cooling of the solvent-free flowable mass, a cohesive film or network composed of particles adhered to each other by the binder composition is obtained.

With the foregoing in mind, it is a feature and advantage of the invention to provide a thin, durable, high absorbent capacity fluid storage material, and a method of making such a fluid storage material wherein particles remain intact on the material even while in a swollen or wet condition.

BRIEF DESCRIPTION OF THE DRAWINGS

These and other objects and features of this invention will be better understood from the following detailed description taken in conjunction with the drawings, wherein.

DEFINITIONS

Figure 1:
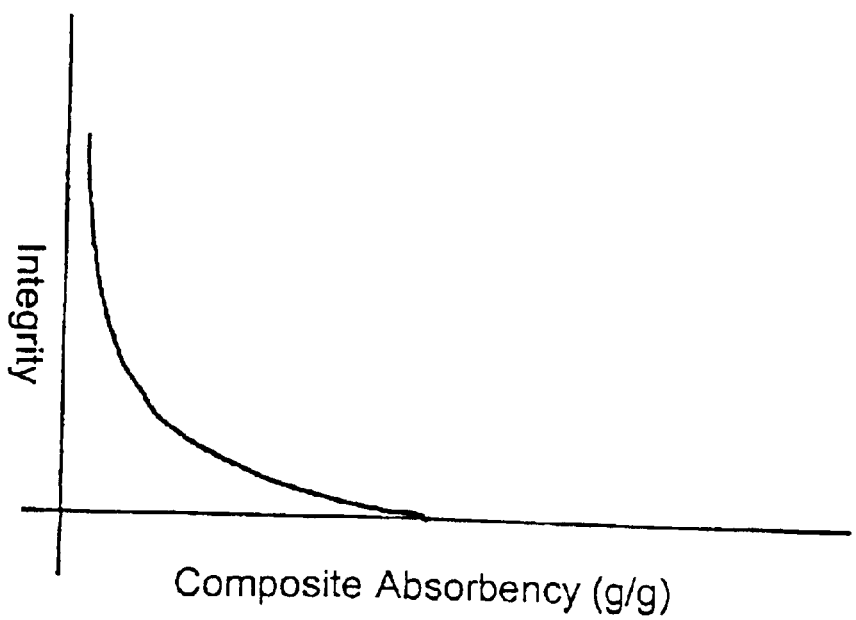
FIG. 1 illustrates an integrity-absorbency relationship of conventional absorbent composites.

Within the context of this specification, each term or phrase below will include the following meaning or meanings.

"Encapsulated" refers to a substance enclosed within a protective coating or membrane.

"Feminine hygiene products" include sanitary pads and napkins, as well as tampons and interlabial feminine hygiene products.

"Fluid" refers to a substance in the form of a liquid or gas at room temperature and atmospheric pressure.

"Fluid storage material" refers to a material that is capable of collecting or absorbing fluids, as well as delivering fluids.

"High density polyethylene (HDPE)" refers to a polyethylene having a density of about 0.95 $g/cm^3$ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to 0.94 $g/cm^3$.

"Low density polyethylene (LDPE)" refers to a polyethylene having long chain branching and a density between about 0.91 and about 0.93 $g/cm^3$.

"Modifying agent" refers to a substance that may be added to a composition to modify the physical properties of the composition, such as the color or texture of the composition.

"Non-absorbent structural layer" or "non-absorbent structural component" or "non-absorbent substrate" refers to a layer or other component, typically lacking absorbent capacity, whose presence in an article contributes to functionally creating the structure of the article.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Particle," "particles," "particulate," "particulates" and the like, refer to a material that is generally in the form of discrete units. The particles can include granules, pulverulents, powders or spheres. Thus, the particles can have any desired shapes such as, for example, cubic, rod-like, polyhedral, spherical or semi-spherical, rounded or semi-rounded, angular, irregular, etc. Shapes having a large greatest dimension/smallest dimension ratio, like needles, flakes, and fibers, are also contemplated for use herein. The use of "particle" or "particulate" may also describe an agglomeration including more than one particle, particulate, or the like.

"Personal care product" includes diapers, diaper pants, training pants, swim wear, absorbent underpants, adult incontinence products, feminine hygiene products, and the like.

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

"Ultra low density polyethylene (ULDPE)" refers to polymers of ethylene and higher alpha-olefin comonomers such as $C_3$–$C_{12}$ comonomers, and combinations thereof, having a density of about 0.86 to less than 0.90 g/cm$^3$.

DESCRIPTION OF PREFERRED EMBODIMENTS

The present invention is directed to a fluid storage material that includes particles secured to one another, and/or secured to a substrate with a crosslinkable binder composition that does not impede absorption or other properties of the particles. The present invention also includes a method of attaching the particles to one another and/or to the substrate, in either wet or dry conditions, such that the particles remain attached to one another and/or to the substrate even while in a swollen or wet condition. Particles secured to one another may form a thin, high density, flexible film or network that can provide the fluid retention function of an absorbent product. Furthermore, a substrate modified by the attachment of superabsorbent particles may be used as a primary absorbent of a product or may add capacity to the product by providing absorbent capacity in components that do not usually have retention capacity.

Figure 2:
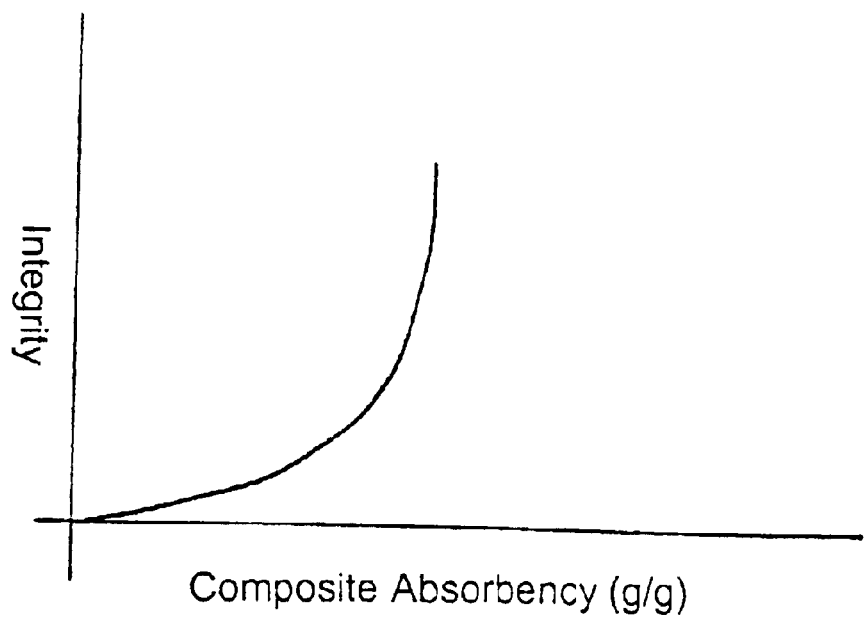
FIG. 2 illustrates an integrity-absorbency relationship of the fluid storage material of the invention.

The fluid storage material of the invention has high mechanical integrity as well as high composite absorbency, relative to conventional absorbent composites containing stabilizing agents. The fluid storage material falls into a region on a right side of a model equation relating integrity to absorbency, thereby exhibiting properties generally not attained by conventional composites. Typically, conventional composites having relatively high absorbency have deficient integrity, while conventional composites having relatively high integrity lack absorbency, as illustrated in FIG. 1. These conventional composites fall into a region on a left side of the model equation. The relationship in FIG. 1 is based on absorbent composites including an absorbent, flexible binder having an absorbent capacity lower than an absorbent capacity of the fibers of the composites, for example 6–7 grams/gram (g/g). This inverse relationship between absorbency and integrity does not hold true for the fluid storage material of the invention containing the binder with an absorbent capacity greater than the fiber absorbent capacity. Instead, the fluid storage material follows the integrity-absorbency relationship illustrated in FIG. 2. The relationship in FIG. 2 is based on fluid storage materials including an absorbent, flexible binder having an absorbent capacity greater than an absorbent capacity of the fibers of the material, for example 6–7 g/g. More specifically, the fluid storage material of the invention suitably has material integrity, or tensile strength, of at least about 8 grams per gsm and an absorbent capacity of at least about 8 g/g, or a tensile strength of at least about 11 grams per gsm and an absorbent capacity of at least about 11 g/g. Alternatively, the fluid storage material may have a tensile strength of at least about 14 grams per gsm and an absorbent capacity of at least about 14 g/g. The tensile strength can be measured using the Strip Tensile Test Method described in U.S. Statutory Invention Registration No. H1,969 issued to Fell on Jun. 5, 2001. The absorbent capacity values can be measured using the Composite Centrifuge Retention Capacity Test described in the test method section below.

Figure 3A:
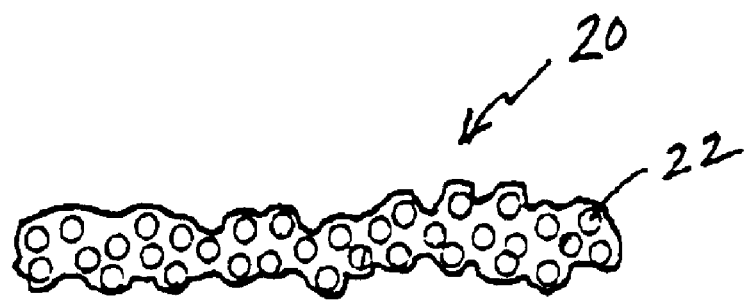
FIGS. 3a and 3b illustrate a representative fluid storage material of the invention without a substrate.
Figure 3B:
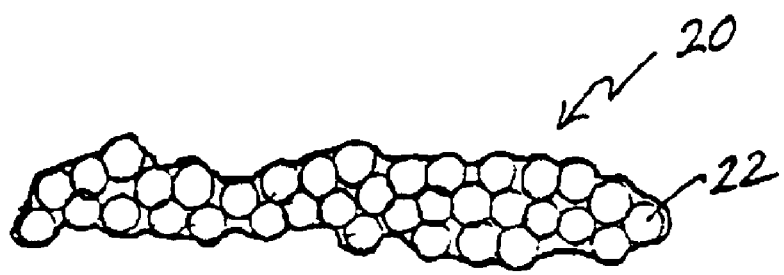

Referring to FIGS. 3a and 3b, a representative example of the fluid storage material 20 of the invention in which particles 22 are secured to one another via a crosslinkable binder composition is illustrated in a dry state (FIG. 3a) and after fluid uptake (FIG. 3b).

Figure 4A:
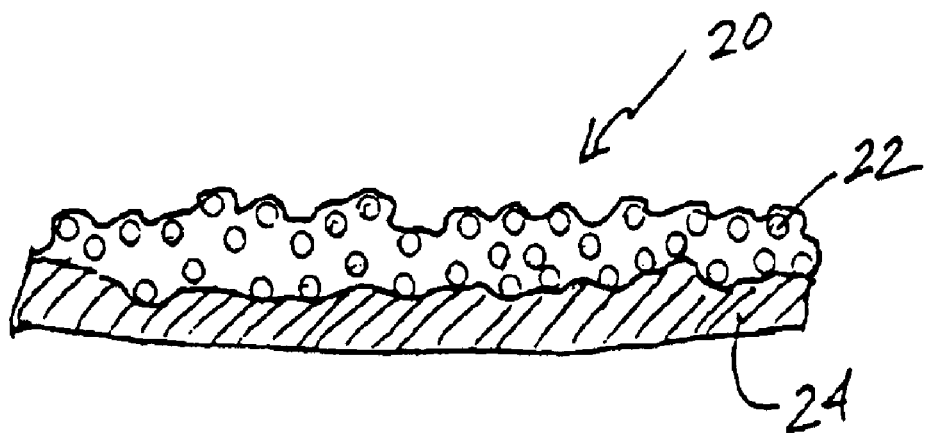
FIGS. 4a and 4b illustrate a representative fluid storage material of the invention with a substrate.
Figure 4B:
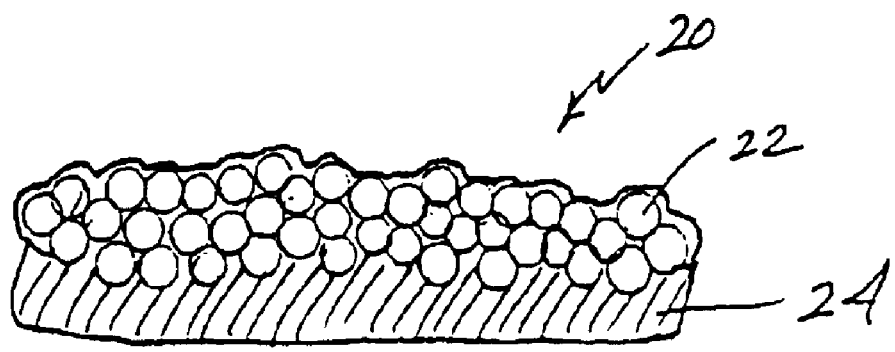

Referring to FIGS. 4a and 4b, a representative example of the fluid storage material 20 of the invention in which particles 22 are secured to a substrate 24 with a crosslinkable binder composition is illustrated in a dry state (FIG. 4a) and after fluid uptake (FIG. 4b). Suitable substrates 24 include, but are not limited to, nonwoven, woven, and knitted fabrics; cellulosic tissue sheets; plastic films, including polypropylene, low density polyethylene, high density polyethylene, linear low density polyethylene, and ultra low density polyethylene; styrene-ethylene-butylene-styrene or styrene-isoprene-styrene block copolymers, KRATON polymers from Kraton Polymers USLLC of Belpre, Ohio, U.S.A., metallocene catalyzed elastomers or plastomers, and the like. Other suitable substrates include monolithic breathable films, such as those made of polyether amide based polymers, for example PEBAX, and ether/ester polyurethane thermal-plastic elastomers; Lycra stranded composites; and elastomer net composites.

In one embodiment the particles 22 are superabsorbent particles (SAP). The SAP may be of any suitable chemistry to provide absorbency under anticipated usage conditions. Suitable chemistries include crosslinked forms of sodium polyacrylate, sodium polymethacrylate, polyacrylamide, carboxymethyl cellulose, grafted starch, poly(sodium aspartate), poly(vinyl amine), poly(dimethyldiallyl amine), chitosan salt, and/or poly(ethylene imine). Superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

Particle size and geometry of the particles may be whatever is suitable for a particular means of applying the particles in solution to the substrate 24 or to a release surface. For example, the particles may be spherical, platelet-like, fibrous, or any related geometry. In the unswollen state, the particles, particularly SAP, may have cross-sectional diameters in a range from about 50 to about 800 microns, or from about 200 to about 400 microns, and for some printing applications from about 60 to about 80 microns, as determined by sieve analysis according to the American Society for Testing Materials (ASTM) Test Method D-1921. It is understood that the particles of material falling within these ranges may include solid particles, porous particles, or may be agglomerated particles including many smaller particles agglomerated into particles within the described size ranges.

In another embodiment, the fluid storage material 20 may include fibers in addition to, or in place of, the particles. Suitable fibers include, but are not limited to, cellulose powder which is obtained by grinding birch (or other) hardwood fiber to a smaller particle size powder in a 0.1 to 0.3 mm range. This powder is available from Functional Food located in Englishtown, N.J. Another suitable fiber is Sulfatate HJ which is a mercerized southern hardwood fiber from Rayonier, located in Jesup Ga. The Sulfatate HJ fiber is about 1.2 millimeters (mm) long and is mercerized. Other hardwood fibers (northern and southern), for example, softwood fibers such as NB-416 from Weyerhaeuser Corporation in Tacoma, Wash., or Foley pulp from Buckeye in Memphis, Tenn., can also be included in the fluid storage material. Chemically stiffened southern softwood pulp may also be included. Examples of suitable cross-linked pulps include highly cross-linked experimental pulp (PXL) from Rayonier, commercially available pulp (NHB-416) from Weyerhaeuser Corporation, and Caressa 1300 pulp from Buckeye. Other suitable fibers include superabsorbent fibers such as FIBERDRI superabsorbent fibers (such as FIBERDRI 1161, FIBERDRI 1231, and FIBERDRI 1241) all available from Camelot Superabsorbent Ltd. of Calgary, Alberta, Canada. Short cut or longer regenerated cellulose fibers, cotton, cellulose acetate, as well as non-cellulosic fibers, such as polyester, acrylic, polyethylene, polypropylene, polyamide, or polylactide fibers are also suitable. Short cut fibers refer to fibers that are cut to less than 4 mm, whereas longer fibers may be cut to intermediate lengths or may be continuous in character.

In yet another embodiment, the particles 22 may be microcapsules including a containment shell and a core of active agent, such as fragrance, odor control agents, cleansing agents, or skin rejuvenation agents, with release of the contents triggered by any appropriate means of breaking the containment shell, such as pressure or exposure to moisture. The containment shell may be made up of polyvinyl alcohol, starch, or any other suitable material. In yet another embodiment, the particles 22 may be a powder, such as an odor-absorbing powder, for example, activated carbon or sodium bicarbonate.

The crosslinkable binder composition includes a soluble crosslinkable binder. Suitable crosslinkable binders are those which provide secure attachment of the particles to one another and/or to the substrate in both a dry state and a wet state, and which are sufficiently hydrophilic to provide uninhibited access of aqueous fluids to the absorbent particles. As a result, the fluid storage material of the invention can be immersed in 0.9% saline solution for 30 minutes with at least 20% of the particles remaining secured to the substrate. Furthermore, at least 30%, or at least 40% of the particles may remain secured to the substrate following immersion. (See Example 5)

The crosslinkable binders may include hydrophilic polymers, or blends of hydrophilic polymers or hydrophobic polymers containing hydrophilic agents. Suitably, the crosslinkable binder composition may include a latent crosslinker composed of multivalent metal ions. An example of a suitable binder includes an alkoxysilane grafted poly (ethylene oxide) ("gPEO") that is soluble in alcohol solvents which do not substantially swell the SAP or other particles, or dissolve the particles. As used herein, the term "substantially swell" refers to a substance that causes a particle to swell, thereby increasing in volume by at least 10%. More specifically, the gPEO, upon exposure to moisture, crosslinks into a gel structure capable of absorbing relatively large amounts of fluids, such as water or saline. This type of binder is capable of crosslinking during the solvent drying or evaporating process to provide enhanced wet attachment. Methacryloxypropyl trimethoxy silane is one example of a suitable alkoxysilane grafting monomer. The particles and binder are suitably present in the binder composition in a ratio ranging from about 1:4 to about 20:1, based on the dry weight of the binder.

Poly(ethylene oxide) ("PEO") is one of a very few polymers that is both water-soluble and thermally processable. PEO has also been shown to be biodegradable under a variety of conditions. Initial work has been done with PEO N-80 (molecular weight~200,000) which is commercially available from Union Carbide. This grade of PEO is suitable for extrusion processing into film.

In accordance with the present invention, PEO is graft polymerized with an organic moiety capable of graft polymerization with PEO which moiety contains a trialkoxy silane functional group or which moiety reacts with water to form a silanol group. The silane graft modified PEO resin can be thermally processed into functional forms, such as films, fibers and foams. When these functional forms are exposed to moisture, a crosslinking reaction occurs, by the mechanism shown below, to provide a gel structure capable of absorbing relatively large amounts of water, such as more than 20 grams of saline per gram of polymer under free swell conditions, making such materials ideal for an absorbent structure.

Water-soluble polymers useful in the present invention include, but are not limited to, poly(alkylene oxides), such as poly(ethylene oxide) ("PEO"), poly(ethylene glycols), block copolymers of ethylene oxide and propylene oxide, poly(vinyl alcohol) and poly(alkyl vinyl ethers). These water-soluble polymers must be capable of graft polymerization with an organic moiety containing a trialkoxy silane functional group or a moiety that reacts with water to form a silanol group. The preferred water-soluble polymer for use in the present invention is PEO.

Graft Polymerization of PEO with
Methacryloxypropyl Trialkoxy Silane Followed by
Exposure to Moisture

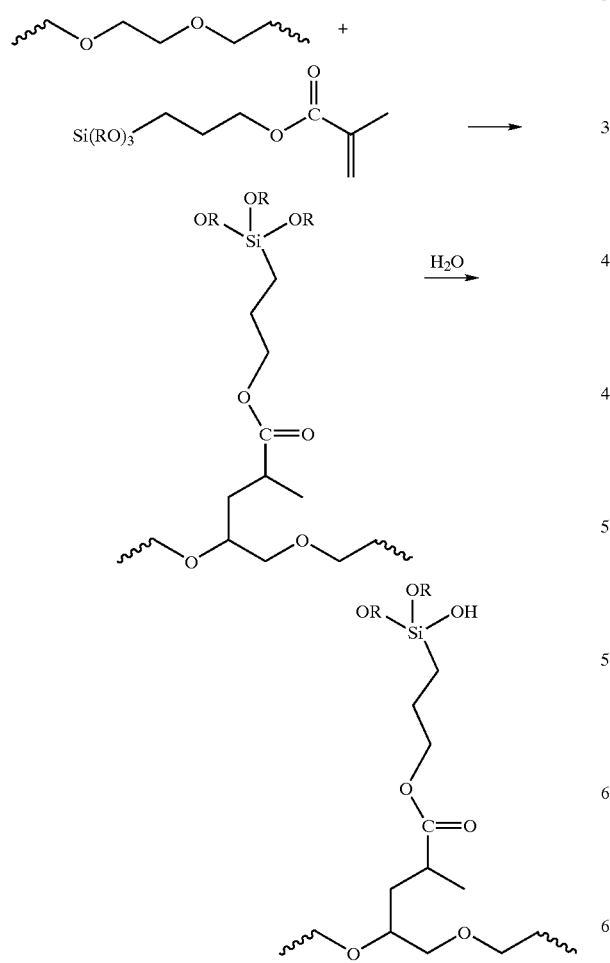

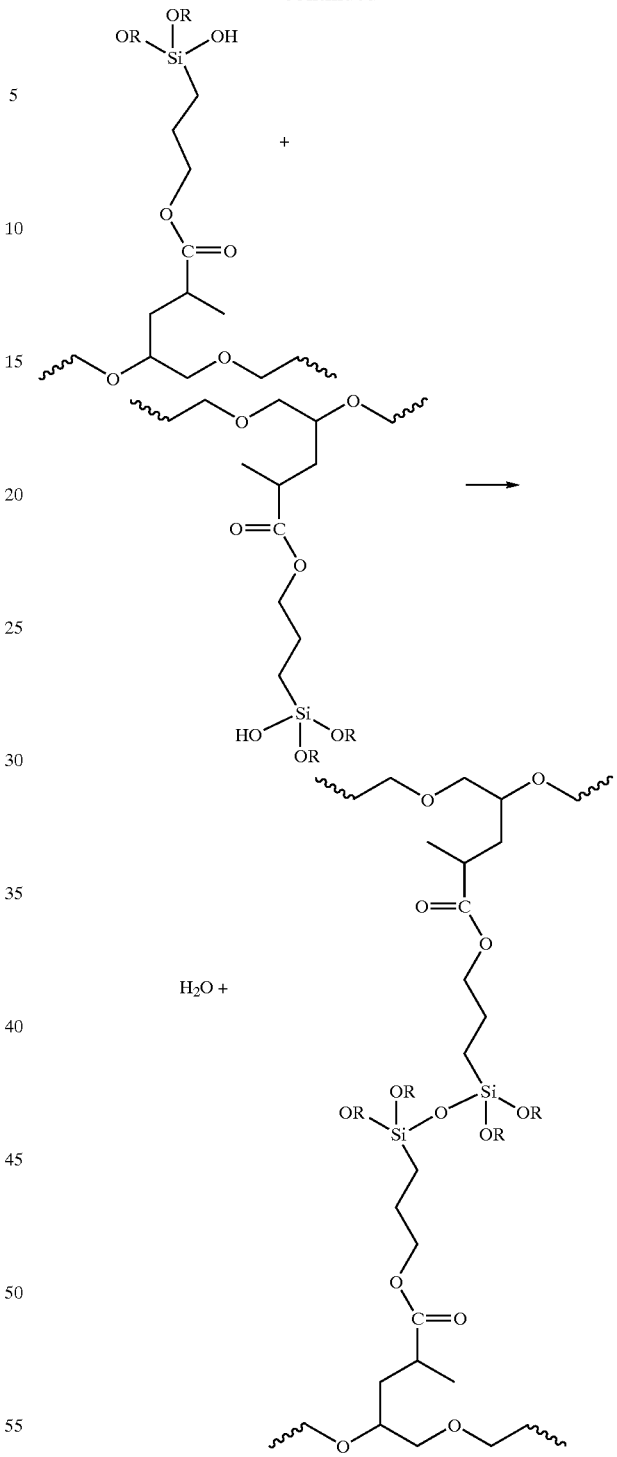

The PEO resins useful for graft modification in accordance with the present invention include, but are not limited to, PEO resins having initial reported approximate molecular weights ranging from about 30,000 g/mol to about 8,000,000 g/mol as determined by rheological measurements. All molecular weights are given on a weight average basis unless otherwise indicated.

Such PEO resins are commercially available from, for example, Union Carbide Corporation having offices in Danbury, Conn., and are sold under the trade designations POLYOX® 205, POLYOX® N-10, POLYOX® N-80, POLYOX® WSR N-750, POLYOX® WSR N-12K and POLYOX® UCARFLOC® Polymer 309.

This invention has been demonstrated by the use of PEO in powder form as supplied by Union Carbide. However, the PEO resins to be modified may be obtained from other suppliers and in other forms, such as pellets. The PEO resins and modified compositions may optionally contain various additives, such as, plasticizers, processing aids, rheology modifiers, antioxidants, UV light stabilizers, pigments, colorants, slip additives, antiblock agents, etc., which may be added before or after modification.

Organic monomers capable of graft polymerization with PEO, which monomers contain a trialkoxy silane functional group or a moiety that reacts with water to form a silanol group, are useful in the practice of this invention. The trialkoxy silane functional group has the following structure:

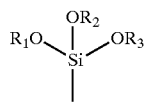

wherein $R_1$, $R_2$ and $R_3$ are alkyl groups independently having from 1 to 6 carbon atoms. The term "monomer (s)" as used herein includes monomers, oligomers, polymers, mixtures of monomers, oligomers and/or polymers, and any other reactive chemical species which is capable of covalent bonding with the parent polymer, PEO. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane, which is commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects to PEO and are effective monomers for grafting in accordance with the present invention.

The amount of organic monomer having trialkoxy silane functional groups or silanol-forming functional groups relative to the amount of PEO may range from about 0.1 to about 20 weight percent of monomer to the weight of PEO. Desirably, the amount of monomer should exceed 0.1 weight percent in order sufficiently to improve the processability of the PEO. Typically, the monomer addition levels are between about 1.0% and about 15% of the weight of the base PEO resin; particularly, between about 1.0% and about 10% of the weight of the base PEO resin; especially, between about 1.5% and about 5.5% of the weight of the base PEO resin for some intended uses. Suitably, the grafting level may be in the range of 0.5 to about 10 weight percent relative to the weight of the PEO.

The binders used in the invention should provide very flexible coatings and should therefore have a glass transition temperature below about 30 degrees Celsius, or below about 10 degrees Celsius, as measured by a Differential Scanning Calorimeter (DSC). The crosslinkable binder composition desirably has a bending modulus lower than the bending modulus of the substrate.

When grafting is achieved by the application of heat, as in a reactive-extrusion process, it is desirable that the initiator generates free radicals through the application of heat. Such initiators are generally referred to as thermal initiators. For the initiator to function as a useful source of radicals for grafting, the initiator should be commercially and readily available, stable at ambient or refrigerated conditions, and generate radicals at reactive-extrusion temperatures.

Compounds containing an O—O, S—S, or N=N bond may be used as thermal initiators. Compounds containing O—O bonds; i.e., peroxides, are commonly used as initiators for graft polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis (cyclohexanecarbonitrile) may be used as the initiator. Examples of commercially available initiators include a liquid, organic peroxide initiator available from R.T. Vanderbilt Company, Inc. of Norwalk, Conn., sold under the trade designation VAROX DBPH peroxide which is a free radical initiator and comprises 2,5-bis(tert butylperoxy)-2, 5-dimethyl hexane along with smaller amounts of di(tert butylperoxide). Other initiators include LUPERSOL® 101 and LUPERSOL® 130 available from Elf Atochem North America, Inc. of Philadelphia, Pa.

A variety of reaction vessels may be useful in the practice of this invention. The modification of the PEO can be performed in any vessel as long as the necessary mixing of PEO, the monomer and the initiator is achieved and enough thermal energy is provided to affect grafting. Desirably, such vessels include any suitable mixing device, such as Brabender Plasticorders, Haake extruders, Bandbury mixers, single or multiple screw extruders, or any other mechanical mixing devices which can be used to mix, compound, process or fabricate polymers. In a desired embodiment, the reaction device is a counter-rotating twin-screw extruder, such as a Haake extruder available from Haake, 53 West Century Road, Paramus, N.J. 07652 or a co-rotating, twin-screw extruder, such as a ZSK-30 twin-screw, compounding extruder manufactured by Werner & Pfleiderer Corporation of Ramsey, N.J. It should be noted that a variety of extruders may be used to modify the PEO in accordance with the invention provided that mixing and heating occur.

Other suitable binders comprise monoethylenically unsaturated carboxylic, sulphonic or phosphoric acids, or salts thereof, and an acrylate or methacrylate ester that contains an alkoxysilane functionality which, upon exposure to water, forms a silanol functional group which condenses to form a crosslinked polymer.

Desired monomers include carboxyl group-containing monomers: monoethylenically unsaturated mono or poly-carboxylic acids, such as (meth)acrylic acid (meaning acrylic acid or methacrylic acid—similar notations are used hereinafter to denote various copolymers), maleic acid, fumaric acid, crotonic acid, sorbic acid, itaconic acid, and cinnamic acid;

Carboxylic acid anhydride group-containing monomers: monoethylenically unsaturated polycarboxylic acid anhydrides (such as maleic anhydride);

Carboxylic acid salt-containing monomers: water-soluble salts (alkali metal salts, ammonium salts, amine salts, etc.) of monoethylenically unsaturated mono- or poly- carboxylic acids (such as sodium (meth)acrylate, trimethylamine (meth)acrylate, triethanolamine (meth)acrylate, sodium maleate, methylamine maleate;

Sulfonic acid group-containing monomers: aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

Sulfonic acid salt group-containing monomers: alkali metal salts, ammonium salts, amine salts of sulfonic acid group containing monomers as mentioned above;

Amide group-containing monomers: vinylformamide, (meth)acrylamide, N-alkyl (meth)acrylamides (such as N-methylacrylamide, N-hexylacrylamide), N,N-dialkyl (meth)acrylamides (such as N,N-dimethylacrylamide, N,N-di-n-propylacrylamide), N-hydroxyalkyl (meth)acrylamides (such as N-methylol (meth)acrylamide, N-hydroxyethyl (meth)acrylamide), N,N-dihydroxyalkyl (meth)acrylamides (such as N,N-dihydroxyethyl (meth)acrylamide), vinyl lactams (such as N-vinylpyrrolidone);

The amount of monoethylenically unsaturated carboxylic, sulphonic or phosphoric acid or salts thereof relative to the weight of the polymeric binder composition may range from about 20 to about 99.9 weight percent. Typically, the monoethylenically unsaturated carboxylic, sulphonic or phosphoric acid or salts thereof levels are between about 25% and about 90% of the weight of the polymeric binder composition; particularly, between about 30% and about 80% of the weight of the polymeric binder composition; especially, between about 50% and about 70% of the weight of the polymeric binder composition for some intended uses.

Organic monomers capable of co-polymerization with monoethylenically unsaturated carboxylic, sulphonic or phosphoric acid or salts thereof, which monomers contain a trialkoxy silane functional group or a moiety that reacts with water to form a silanol group, are useful in the practice of this invention. The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example but not limited to, (3-chloropropyl)trimethoxysilane. An alcohol group incorporated into the co-polymer may subsequently be reacted with, for example but not limited to, trimethoxysilane.

The amount of organic monomer having trialkoxy silane functional groups or silanol-forming functional groups relative to the weight of the polymeric binder composition may range from about 0.1 to about 15 weight percent. Desirably, the amount of monomer should exceed 0.1 weight percent in order provide sufficient crosslinking upon exposure to moisture. Typically, the monomer addition levels are between about 1.0% and about 15% of the weight of the polymeric binder composition; particularly, between about 1.0% and about 10% of the weight of the polymeric binder composition; especially, between about 1.5% and about 5.5% of the weight of the polymeric binder composition for some intended uses.

Optionally, the polymeric binder may include long chain, hydrophilic monoethylenically unsaturated esters, such as poly(ethylene glycol) methacrylate having from 1 to 13 ethylene glycol units, particularly, between 2 and 10 ethylene glycol units; especially, between 3 and 6 ethylene glycol units. The hydrophilic monoethylenically unsaturated esters have the following structure:

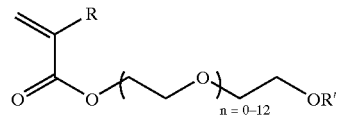

R' =H, alkyl, phenyl

Suitable acrylic acid salts for use in combination with poly(ethylene glycol) methacrylate include sodium acrylate, potassium acrylate, ammonium acrylate, and quaternary amine acrylate.

The amount of monoethylenically unsaturated hydrophilic esters relative to the weight of the polymeric binder composition thereof may range from about 0 to about 75 weight percent of monomer to the weight of the polymeric binder composition. Typically, the monomer addition levels are between about 10% and about 60% of the weight of the polymeric binder composition; particularly, between about 20% and about 50% of the weight of the polymeric binder composition; especially, between about 30% and about 40% of the weight of the polymeric binder composition for some intended uses.

In one embodiment, the polymeric binder composition is prepared by adding a solution of the above monomers to an initiator solution, at a suitable temperature to generate free radicals. An initiator solution may be prepared by dissolving an initiator in a solvent. Possible solvents include, but are not limited to, alcohols such as ethanol. A variety of initiators may be useful in the practice of this invention. The polymerization initiator may be activated using a variety of methods including, but not limited to, thermal energy, ultraviolet light, redox chemical reactions. Suitable classes of initiators are organic peroxides and azo compounds, with benzoyl peroxide and azobisisobutyronitrile (AIBN) as examples.

Suitable solvents for the binder composition include any solvents that provide for solubility of the binder without swelling the particles, such that the dry weight of the particles is increased by no more than 10% as a result of imbibing solvent. Alternatively, no more than 1% by weight gain resulting from solvent is imbibed by the particles. The amount of solvent may be chosen to provide the appropriate flow properties for the particle/binder blend which is appropriate for the chosen application process. As mentioned, alcohol solvents may be used in the binder composition. In one embodiment, the alcohol solvent may include between about 99.5% and about 50% alcohol by weight, and between about 0.5% and about 50% water by weight. Ethanol is one example of a suitable alcohol solvent.

In addition, modifying agents such as compatible polymers, plasticizers, colorants, stabilizers, flow aids, and preservatives may be incorporated in the binder composition.

Alternatively, the polymeric binder composition is prepared by polymerization without solvent in a suitable vessel. The polymerization initiator may be activated using a variety of methods including, but not limited to, thermal energy, ultraviolet light, redox chemical reactions. Suitable classes of initiators are organic peroxides and azo compounds.

The fluid storage material 20 may be made by first dispersing the particles 22 in the binder composition solution, and applying the blend of particles in the binder composition to the substrate 24 or to a release surface (when no substrate is included in the finished material 20). The particle blend may be applied to the substrate or release surface using any suitable application process, including knife over roll coating, or roll coating, either in a continuous coverage or a patterned coverage. Printing applications are other suitable application techniques, including gravure printing, screen, and jet printing. The particle blend may also be applied to the substrate or release surface using a spray application. Alternatively, the binder composition may be heated to a flowable condition and extruded onto the substrate or release surface. The particles may be added to the binder composition either prior to extrusion coating the flowable binder composition or subsequent to extrusion coating the flowable binder composition onto the substrate or release surface. The particles may be pressed into the binder composition once the binder composition is on the substrate or release surface.

Once the particles are applied to the substrate or release surface, crosslinking of the binder is induced by any suitable method. This may occur before, during, or after removal of part or all of the solvent. For example, the crosslinking may be induced through thermal initiation, radiation initiation (including ultraviolet, microwave, and electron-beam), and redox chemical reactions. A preferred crosslinking method is moisture-induced crosslinking by hydrolysis and condensation of alkoxysilanes. Crosslinking by this method can take place during solvent removal or after solvent removal by exposure to air at ambient humidity. Solvent may be removed from the substrate or release surface, either by evaporating the solvent or any other suitable technique. Recovery of the solvent is a part of the process and methods for this are widely known to those skilled in the art.

In this invention, formation of covalent bonds between the particles and the binder is not the major means of attachment. Instead, a membrane film is formed around the particles. The membrane film surrounds the particles and penetrates the substrate (if present). This membrane film or coating crosslinks with itself and, since it penetrates into porous substrates, the coating provides attachment to other particles and/or to the substrate, in the wet and dry state, by means of entanglement. In some cases the coating may form covalent silol ether bonds with hydroxyl groups of a substrate such as cellulose. The properties of the membrane film include water permeability and absorbency. Desirably, the membrane can absorb more than 0.8 grams of 0.9% saline solution per gram of coating material. Furthermore, it is desirable for the coating membrane to swell laterally as it absorbs fluid to create a larger membrane such that the particles, upon absorbing fluid, can grow in volume without restriction from the membrane coating. The resulting fluid storage material maintains high flexibility since the crosslinkable binder composition provides strength to the substrate without increasing stiffness.

The fluid storage material 20 of the invention provides an advantage of additional utilization of the structural components of personal care absorbent articles as carriers of absorbent capacity, and/or other functionalities. By adding absorbency to typically non-absorbent structural components, additional utility can be added to such structural components as carriers of absorbent capacity. This added capability provides for thinner, more conformable products having greater absorbent capacity. Suitably, the fluid storage material 20 in which the particles 24 are crosslinked to one another without a substrate 24 has an absorbent capacity of at least 5 grams per gram (g/g), or at least 10 g/g, or at least 15 g/g according to the teabag test method described below, and a density of at least 0.5 grams per cubic centimeter ($g/cm^3$), or at least 0.7 $g/cm^3$, or at least 0.9 $g/cm^3$, and a Gurley stiffness value of less than 320 milligrams (mg), or less than 160 mg, or less than 60 mg. The fluid storage material 20 in which the particles 24 are connected through the binder matrix to a substrate 24 as well as possibly to one another has an absorbent capacity, as measured by the AULC test method described below, of at least 0.2 grams per square centimeter ($g/cm^2$), or at least 0.6 $g/cm^2$, or at least 1.0 $g/cm^2$ under an applied load of 0.3 pounds per square inch (psi) according to the absorbency under load test method described below, and a density of at least 0.1 $g/cm^3$, or at least 0.4 $g/cm^3$, or at least 0.7 $g/cm^3$, and a Gurley stiffness value of less than 400 mg, or less than 200 mg, or less than 100 mg.

Figure 6:
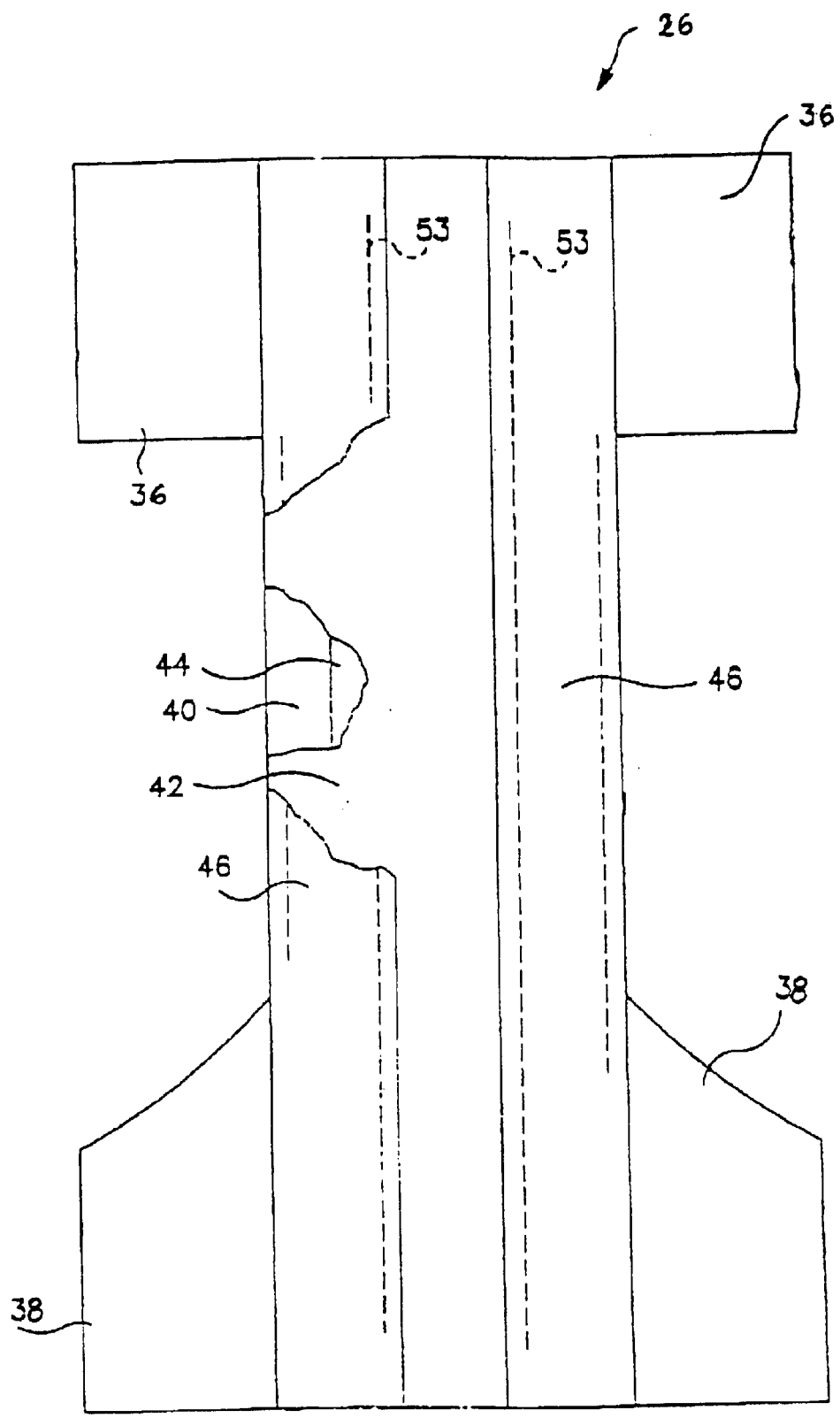
FIG. 6 is a plan view of the training pant of FIG. 5 in a partially disassembled, stretched flat state, and showing the surface of the garment that faces the wearer when the article is worn, and with portions cut away to show underlying features.
Figure 7:
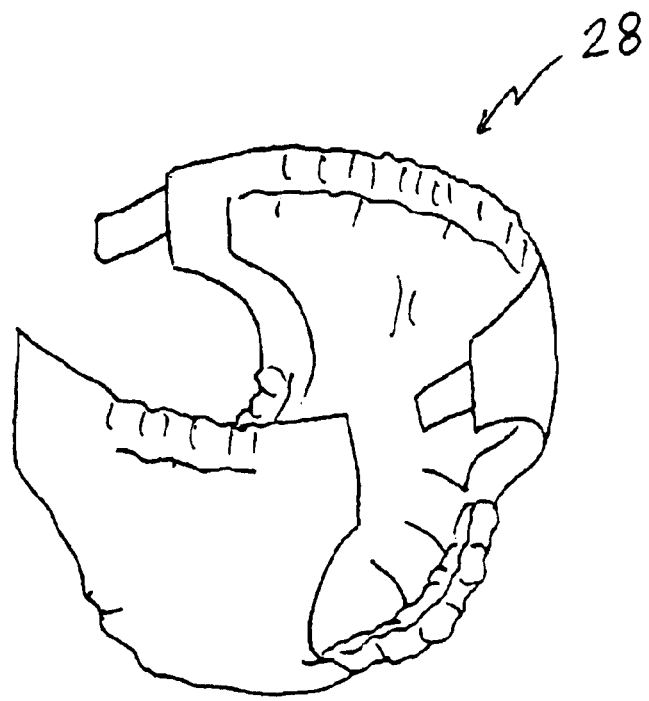
FIG. 7 is a perspective view of a diaper having the fluid storage material of the invention incorporated therein.
Figure 8:
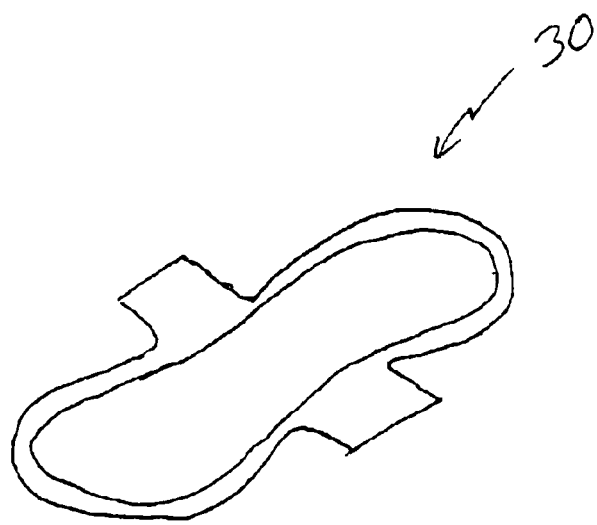
FIG. 8 is a perspective view of a feminine hygiene product having the fluid storage material of the invention incorporated therein.
Figure 9:
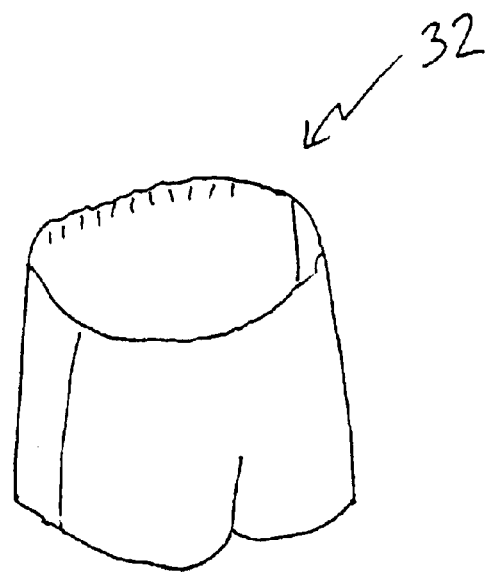
FIG. 9 is a perspective view of a child's swim pant having the fluid storage material of the invention incorporated therein.
Figure 10:
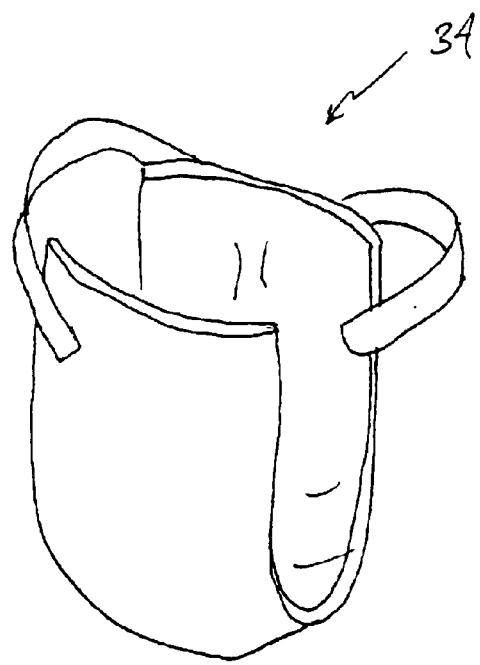
FIG. 10 is a perspective view of an adult incontinence product having the fluid storage material of the invention incorporated therein.

The fluid storage material 20 of the invention can be incorporated into any suitable absorbent article. The fluid storage material 20 of the invention is particularly suitable for absorbing liquids such as urine, menses, or sweater, or gases, especially malodorous gases. Examples of suitable articles that may include the fluid storage material 20 include training pants 26 (FIGS. 5 and 6), diapers 28 (FIG. 7), diaper pants, feminine hygiene products 30 (FIG. 8), swimwear 32 (FIG. 9), incontinence products 34 (FIG. 10), other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of the fluid storage material incorporated into a child's training pant 26.

Figure 5:
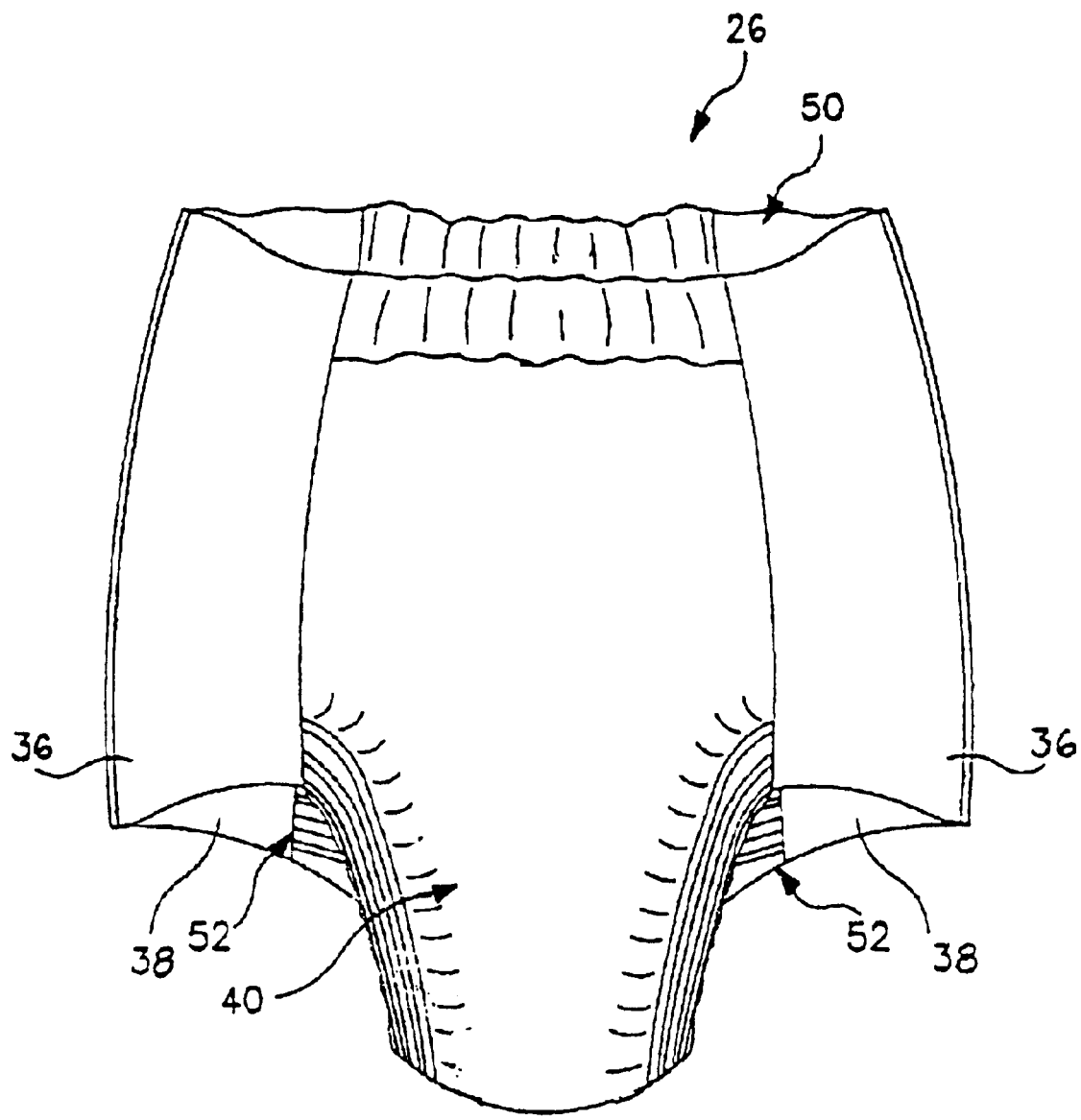
FIG. 5 is a perspective view of a child's training pant having the fluid storage material of the invention incorporated therein.

As shown in FIG. 5, a training pant 26 having permanently bonded sides, or a training pant having refastenable sides in a fastened position, defines a three-dimensional pant configuration having a waist opening 50 and a pair of leg openings 52. The training pant 26 includes a body side liner 42 which is configured to contact the wearer, and an outer cover 40 opposite the body side liner which is configured to contact the wearer's clothing. An absorbent assembly 44 (FIG. 6) is positioned or located between the outer cover 40 and the body side line 42. The body side liner 42 and the outer cover 40 are both non-absorbent structural components, lending shape to the training pant 26, while the absorbent assembly 44 is provided to absorb and contain bodily exudates. In one embodiment of the invention, any of the materials of the outer cover 40 and/or body side liner 42 can be converted into or replaced with the fluid storage material 20 of the invention. Alternatively, or in addition, the material 20 of the invention may be inserted into the garment as a layer of retention material.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable breathable material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain non-breathable elastic films can also be used to make the outer cover 40. Examples of suitable non-breathable films can be made of styrene-ethylene-butylene-styrene or styrene-isoprene-styrene block copolymers, KRATON polymers from Kraton Polymers USLLC of Belpre, Ohio, U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the wearer's skin. Further, the body side liner 42 can be less hydrophilic than the absorbent assembly 44, to present a relatively dry surface to the wearer and permit liquid to readily penetrate through its thickness.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL N-62 available from available from Uniqema Inc., a division of ICI of New Castle, Del., U.S.A. and GLUCOPON 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

The absorbent assembly 44 can be any structure which is generally compressible, conformable, non-irritating to the wearer's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with SAP. Under one aspect of the present invention, the primary absorbent assembly 44 can be the fluid storage material 20.

The training pant 26 can also incorporate other materials that are designed primarily to receive, temporarily store, and/or transport liquid along the mutually facing surface with the absorbent assembly 44, thereby maximizing the overall absorbent capacity of the absorbent assembly 44, but additional layers add additional bulk to the garment. As one embodiment, this temporary storage layer may be made to have permanent storage capacity by the present invention without loss of its current function. This would allow a reduction in the mass of the primary absorbent component. One or more of the non-absorbent structural components already included in the garment can be made of the fluid storage material 20 of the invention, thereby providing absorbent capacity in typically non-absorbent or low-absorbent features without the added bulk of an additional layer. Alternatively, the inclusion of one or more such components made of the fluid storage material 20 can permit a reduction in the amount or size of the primary absorbent assembly 44, resulting in a higher total product retention capacity.

Additional non-absorbent structural components in the training pant 26 may include a pair of transversely opposed front side panels 36, and a pair of transversely opposed back side panels 38. The side panels 36, 38 may be integrally formed with the outer cover 40 and/or the body side liner 42, or may include two or more separate elements. Suitable materials for side panels, as well as processes of incorporating side panels into a training pant, are known and are described, for example, in U.S. Pat. No. 4,940,464 issued Jul. 10, 1990 to Van Gompel et al., which is incorporated herein by reference. In one embodiment of the invention, the materials typically used to make the side panels 36, 38 may be used as the substrate to form the fluid storage material 20 of the present invention, thus the side panels 36, 38 may be made from the fluid storage material 20 of the invention.

Other non-absorbent structural components in the training pant 26 may include a pair of containment flaps 46 which are configured to provide a barrier to the transverse flow of any body exudates discharged from the wearer. A flap elastic member 53 (FIG. 6) may be operatively joined with each containment flap 46 in any suitable manner as is well known in the art. The elasticized containment flaps 46 define an unattached edge which assumes an upright, generally perpendicular configuration in at least a crotch region of the training pant 20 to form a seal against the wearer s body. The containment flaps 46 can be located along transversely opposed side edges of the training pant 20, and can extend longitudinally along the entire length of the training pant or may only extend partially along the length of the training pant. Suitable constructions and arrangements for the containment flaps 46 are generally well known to those skilled in the art. Similar to the side panels 36, 38, the materials typically used to make the containment flaps 46 may be used as the substrate to form the fluid storage material of the invention, thus the containment flaps 46 may be made from the fluid storage material of the invention.

The structural components of the garment made up of the fluid storage material 20 of the invention suitably have a thickness of between about 0.2 and about 4 millimeters (mm), or between about 0.5 and about 3.0 mm, or between about 1.0 and about 2.5 mm, as measured at 0.05 psi, and an absorbent capacity of between about 0.1 and about 1.8 g/cm$^2$, or between about 0.5 and about 1.4 g/cm$^2$, or between about 0.7 and about 1.1 g/cm$^2$ under an applied load of 0.3 psi. The absorbent capacity of the material can be measured according to the test method described in detail below.

By adding absorbent capacity to components that typically have minimal absorbent capacity, the material of the invention can be used to create personal care articles, or other types of absorbent articles, that are thinner and/or more absorbent than conventional absorbent articles.

EXAMPLES

Example 1

A 2% solution of poly(ethylene oxide), grafted with 6 wt % methacryloxypropyl trimethoxy silane, was prepared by agitation of 4 grams of resin pellets with an Ultraturrax homogenizer in 196 grams of a solvent composed of 95 wt % methanol/5 wt % water. 20 grams of FAVOR® 880 superabsorbent polymer (SAP) was added to the solution and agitated for five minutes. A portion of the SAP was filtered with a fritted glass filter under lab vacuum to obtain a moist cake of SAP that was dried at room temperature for 16 hours to provide a superabsorbent coated with crosslinked poly(ethylene oxide) (PEO). A portion of the SAP in solution was applied, with a paintbrush, to the surface of a paper towel (currently available SCOTT® Towel, manufactured by Kimberly-Clark Corporation of Neenah, Wis.). The solvent was evaporated at room temperature for several days. In the same manner, a portion of the binder solution without SAP was applied to a paper towel and dried.

Uncoated SAP, the coated SAP, the paper towel coated with crosslinked binder, and the towel coated with SAP and crosslinked binder were tested for absorbency under an applied load of 0.3 psi, in accordance with the test method described below. The results are shown in Table 2.

TABLE 1

Absorbency Under Load Zero Load (AUZL) Test Results

| Material | AUZL (grams/gram) |
|---|---|
| Uncoated FAVOR 880 SAP | 37.7 |
| FAVOR 880 SAP coated with crosslinkable binder from Example 1 | 36.5 |

TABLE 2

Absorbency Under Load Test Results

| Material | Load applied (psi) | Absorbency (g/g of SAP/ binder coating) | Absorbency (g/cm$^2$ of fluid storage material) |
|---|---|---|---|
| Crosslinked PEO binder applied to paper towel | 0.3 | 19.6 | 0.035 |
| Crosslinked PEO binder & SAP applied to paper towel | 0.3 | 18.1 | 0.37 |

These results indicate: (1) that coating the superabsorbent with the crosslinked PEO binder has minimal impact on the absorbent properties of the SAP; (2) the crosslinked binder has suitable absorbent properties without the addition of SAP; and (3) the use of the crosslinked binder to secure SAP to the paper towel provides an absorbent web with good fluid retention capability.

Example 2

An initiator solution was prepared by dissolving 0.345 grams benzoyl peroxide in 300 ml methanol. A monomer solution was prepared by mixing 23.1 grams acrylic acid (23 weight %), 69.3 grams poly(ethylene glycol) methyl ether methacrylate (70 weight %), and 7.3 grams 3-(trimethoxysilyl)propyl methacrylate (7 weight %) in 300 ml methanol. The initiator solution was heated in a jacketed reactor to 64 degrees Celsius with stirring. The monomer solution was added dropwise to the initiator solution. The resulting polymerization solution was stirred and heated at 64 degrees Celsius for approximately 2 hours at which time a solution of 0.0953 grams azobisisobutyronitrile (AIBN) in 30 ml methanol was added. Stirring and heating at 64 degrees Celsius was continued for an additional one hour at which time a second solution of 0.0953 grams AIBN in 30 ml methanol was added to the polymerization solution. After stirring and heating at 64 degrees Celsius for one more hour a third and final solution of 0.0953 grams AIBN in 30 ml methanol was added to the polymerization solution. Approximately 1.5 hours after addition of the third AIBN solution a portion of the polymerization solvent was distilled off. The total heating time for the polymerization was approximately 6 hours and 45 minutes. The resulting solution was found, after removal of the methanol, to be 19% polymer by weight. A sample of the binder solution was dried in a hood at room temperature. The resultant film was soft and flexible and had absorbent capacity of 0.93 g/g. This film had a glass transition temperature of −49 degrees Celsius, as measured by differential scanning calorimetry (DSC).

Another portion of this binder solution was neutralized with sodium hydroxide solution such that 50% of the acrylic acid units were in the sodium salt form. The neutralized binder solution produced a soft, flexible film after drying at room temperature. This film had absorbent capacity of 1.7 g/g, as measured by the Absorbent Capacity test method described below, and a glass transition temperature of −44 degrees Celsius.

To 61 grams of the solution above was added 30 grams of polyacrylate superabsorbent designated FAVOR 9543, manufactured at Stockhausen, Inc., Greensboro, N.C. The particle size was segregated by sieving and utilizing the fraction that passed through a 300 micron screen. This mixture was stirred to provide a homogeneous suspension of the particles in the binder solution. The mixture was spread evenly onto a 20×20 cm piece of wet-laid tissue with a spatula. The tissue web was prepared using the Uncreped Through-Air Dried (UCTAD) process as described in U.S. Pat. Nos. 5,656,132 and 5,932,668. The tissue web was composed of Sulfatate HJ fibers (80% by weight), available from Rayonier and 20% by weight of LL=19 fibers, available from Kimberly-Clark Inc., Terrace Bay, Ontario, Canada, and had a basis weight of 100 grams per square meter.

The methanol solvent was evaporated in a hood, at room temperature, over 10 hours. The dry coating weight of the SAP/binder mixture was found to be 550 grams per square meter and composed of 72% SAP and 28% binder polymer. The coated tissue had a dry thickness of 1.3 mm. The coated tissue web had about the same flexibility as the uncoated web and the SAP was securely attached to the web, even with rubbing under light pressure.

The absorbency under loads of 0.01, 0.3, and 0.9 psi was measured according to the AULC test method described below. The results, adjusted to the average coating weight, are shown in Table 3.

TABLE 3

Absorbency Under Load on Composite (AULC) Test Results

| Load applied (psi) | Absorbency (g/g of SAP/ binder coating) | Absorbency (grams per square cm of fluid storage material) |
| --- | --- | --- |
| 0.01 | 15.6 | 0.9 |
| 0.3 | 16.2 | 0.8 |
| 0.9 | 15.8 | 0.9 |

This example demonstrates the capability to make thin, flexible, high capacity absorbent with high integrity in the dry state and the ability to hold the swollen SAP in place after absorbing fluid.

Example 3

An initiator solution was prepared by dissolving 0.354 grams benzoyl peroxide in 300 milliliters of ethanol. The monomer solution was prepared by mixing 24.15 grams of acrylic acid (24 mass %), 73.5 grams of poly(ethylene glycol) methyl ether methacrylate (74 mass %) and 1.46 grams of 3-(trimethoxysilyl)propyl methacrylate (2 mass %) in 250 milliliters of ethanol. The initiator solution was heated in a jacketed reactor to 75 degrees Celsius with stirring. The monomer solution was added dropwise to the initiator solution. The polymerization solution was stirred and heated at 75 degrees Celsius for approximately 2 hours at which time a solution of 0.096 grams azobisisobutyronitrile (AIBN) in 30 ml ethanol was added. Stirring and heating at 75 degrees Celsius for an additional hour at which time a second solution of 0.096 grams AIBN in ethanol was added to the polymerization solution. A third addition of 0.096 grams AIBN in ethanol was made after one more hour at 75 degrees Celsius. Stirring and heating continued at 75 degrees Celsius for a total reaction time of about 7 hours. The reactor was cooled to 20 degrees Celsius and the solution was stirred under nitrogen atmosphere overnight. This binder polymer is designated 3a. A portion of the polymer solution was dried for 16 hours at room temperature to create a sticky, water-absorbent film. The polymer concentration of the solution was 16.2% by weight.

A portion of the polymer solution was treated with sodium hydroxide solution to neutralize a portion (50%) of acrylic acid units in the binder polymer in order to increase the absorbency of the crosslinked film generated by drying the solution. The neutralization was done by adding 5.25 grams of a 48.5% sodium hydroxide solution to 236 grams of polymer solution 3a (16.2% polymer) and stirring at room temperature for 5 minutes. The neutralized binder polymer is designated 3b.

To 60 grams of the solution 3a was added 30 grams of polyacrylate superabsorbent designated FAVOR 9543, manufactured at Stockhausen, Inc., Greensboro, N.C. The particle size was segregated by sieving and utilizing the fraction that passed through a 300 micron screen. This mixture was stirred to provide a homogeneous suspension of the particles in the binder solution. The mixture was spread evenly onto a 20×20 cm piece of wet-laid tissue with a spatula. The tissue web was prepared using the Uncreped Through-Air Dried (UCTAD) process as described in U.S. Pat. Nos. 5,656,132 and 5,932,668. The tissue web was composed of Sulfatate HJ fibers (80% by weight), available from Rayonier and 20% by weight of LL=19 fibers, available from Kimberly-Clark Inc., Terrace Bay, Ontario, Canada. The tissue web had a basis weight of 100 grams per square meter. The same procedure was used with solution 3b. The ethanol solvent was evaporated in a hood, at room temperature, over 10 hours.

The average dry coating weight of the SAP/binder mixture with solution 3a was found to be 386 grams per square meter and composed of 76% SAP and 24% binder polymer. The coated tissue had a dry thickness of 1.0 mm. The coated tissue web had about the same flexibility as the uncoated web and the SAP was securely attached to the web, even with rubbing under light pressure.

The average dry coating weight of the SAP/binder mixture with solution 3b was found to be 423 grams per square meter and composed of 71% SAP and 29% binder polymer. The coated tissue had a dry thickness of 1.0 mm. The tissue web coated with solution 3b was slightly stiffer than the tissue web coated with solution 3a. SAP was securely attached to the web, even with rubbing under light pressure.

The absorbency under loads of 0.01, 0.3, and 0.9 psi was measured according to the AULC test method described below. The results, adjusted to the average coating weight, are shown in Tables 4 and 5.

TABLE 4

Absorbency Under Load Test Results for Binder 3a

| Load applied (psi) | Absorbency (g/g of SAP/ binder coating) | Absorbency (grams per square cm of fluid storage material) |
| --- | --- | --- |
| 0.03 | 15.2 | 0.6 |
| 0.3 | 12.8 | 0.5 |
| 0.9 | 15.4 | 0.5 |

TABLE 5

Absorbency Under Load Test Results for Binder 3b

| Load applied (psi) | Absorbency (g/g of SAP/ binder coating) | Absorbency (grams per square cm of fluid storage material) |
| --- | --- | --- |
| 0.03 | 20.0 | 0.8 |
| 0.3 | 16.5 | 0.6 |
| 0.9 | 14.0 | 0.6 |

These results indicate that partial neutralization of the acrylic acid within the binder polymer results in higher absorbency, but also slightly higher stiffness.

Example 4

The polymerization procedure described in Example 3 was repeated to prepare polymer binder 4. To 100 grams of binder solution 4, at 17.4% polymer, was added 25 grams of water.

To 25 grams of the water-diluted solution 4 was added 10 grams of polyacrylate superabsorbent designated FAVOR 9543, manufactured at Stockhausen, Inc., Greensboro, N.C. The particle size was segregated by sieving and utilizing the fraction that passed through a 300 micron screen. This mixture was stirred to provide a homogeneous suspension of the particles in the binder solution. The mixture was spread evenly onto an 8×34 cm piece of a high loft bonded carded web with a spatula. The high loft bonded carded web is surge material made according to U.S. Pat. No. 5,364,382, manufactured by Kimberly-Clark. The basis weight of the surge material was 85 gsm and the density was 0.04 g/cm$^3$, as measured at a pressure of 0.05 psi.

The average dry coating weight of the SAP/binder mixture with solution 4 was found to be 571 grams per square meter and composed of 74% SAP and 26% binder polymer. The coated surge had a dry thickness of 2.8 mm. The surge web coated with solution 4 remained flexible and the SAP was securely attached to the web, even with rubbing under light pressure.

TABLE 6

Absorbency Under Load Test Results for Binder 4

| Load applied (psi) | Absorbency (g/g of SAP/ binder coating) | Absorbency (grams per square cm of fluid storage material) |
| --- | --- | --- |
| 0.03 | 18.5 | 1.0 |
| 0.3 | 18.2 | 1.0 |
| 0.9 | 12.1 | 0.7 |

These results indicate SAP can be securely attached to a high loft nonwoven and provide high levels of absorbency and flexibility.

Example 5

This Example is a comparative example of the attachment of SAP in excess fluid. In order to determine the efficiency of the crosslinked binder to hold superabsorbent particles onto a substrate, even in the presence of excess fluid, the following test was conducted. A surge web coated with SAP/binder was used to measure attachment efficiency and was compared to a surge web coated with the same SAP but with a non-crosslinked (water soluble) binder. The SAP/binder coated surge was prepared as follows. To 25 grams of the water-diluted solution 4 was added 10 grams of polyacrylate superabsorbent designated FAVOR 880, manufactured at Stockhausen, Inc., Greensboro, N.C. This mixture was stirred to provide a homogeneous suspension of the particles in the binder solution. The mixture was spread evenly onto an 8 centimeter (cm) by 34 cm piece of a high loft bonded carded web with a spatula. The high loft bonded carded web was surge material made according to U.S. Pat. No. 5,364,382, manufactured by Kimberly-Clark. The basis weight of the surge material was 85 gsm. A second sample was prepared in the same manner except that a second layer of surge material was applied on top of the coating to create a "sandwich" structure.

The dry weight of a 28 cm by 9 cm sample of SAP/binder coated surge was measured and then the web was suspended above a 4 liter beaker. The beaker was filled with 0.9% saline solution and placed on a stir plate (Cole Parmer model 4658 stir hot plate available from Cole Parmer Instrument Co., Chicago, Ill.) with a 3 inch stir bar, 0.5 inch in diameter. The coated web immersed in fluid was stirred for 30 minutes at a setting of 5 (low). An additional test was run in the same manner at a setting of 10 (high). The coated surge material was removed from solution and dried completely. The re-dried weight was compared to the original dry weight to determine the percent of SAP/binder that was removed in the given test condition. The percentage of SAP/binder remaining on the surge material was calculated by subtracting the percentage of SAP/binder removed from 100%.

As a comparative sample, the surge was coated with a non-crosslinked binder prepared by mixing 20 g of POLYOX N-10 and 20 g of POLYOX 205 (both available from Union Carbide, Danbury, Conn.) in a mixture of 300 g methanol and 40 g water to provide a 9.5% solution. 7.5 grams of FAVOR 9543 polyacrylate superabsorbent was mixed with 26.3 grams of this solution to provide a 3:1 SAP to binder ratio. This mixture was coated onto the surge material made according to U.S. Pat. No. 5,364,382, and dried as described in Example 4. The resultant coated surge was tested in the same manner in excess 0.9% saline as described above. The results are shown in Table 7.

TABLE 7

Attachment of SAP in Excess Fluid

| Sample | Agitation | Percent SAP/binder Remaining |
|---|---|---|
| 6A | None | 40 |
| 6B | Low | 45 |
| 6C | High | 30 |
| 6D | None | 66 |
| 6E | Low | 49 |
| 6F | High | 42 |
| Comparative A | None | 4 |
| Comparative B | Low | 6 |
| Comparative C | High | 4 |

Samples 6A–C were the surge material coated with a single layer of SAP and binder from this invention.

Samples 6D–E were the same as A–C except that a second layer of surge material was applied on top of the coating to create a "sandwich" structure.

Comparatives A–C were the surge material coated with a single layer of SAP and the non-crosslinked comparative binder described above.

This example demonstrates that the crosslinked binder of this invention significantly improves the attachment of the SAP to a substrate, even when exposed to a large excess of fluid.

Example 6

An initiator solution was prepared by dissolving 0.354 grams benzoyl peroxide in 300 milliliters of ethanol. A monomer solution was prepared by mixing 21.4 grams of acrylic acid (24 mass %), 73.5 grams of poly(ethylene glycol) methyl ether methacrylate (74 mass %) and 1.46 grams 3-(trimethoxysilyl)propyl methacrylate (2 mass %) in 250 milliliters of ethanol. The initiator solution was heated in a jacketed reactor to 75 degrees Celsius with stirring. The monomer solution was added dropwise to the initiator solution. The polymerization solution was stirred and heated at 75 degrees Celsius for approximately 2 hours at which time a solution of 0.096 grams azobisisobutyronitrile (AIBN) in 30 ml ethanol was added. Stirring and heating at 75 degrees Celsius for an additional hour at which time a second solution of 0.096 grams azobisisobutyronitrile (AIBN) in 30 ml ethanol was added to the polymerization solution. A third addition was made after one more hour at 75 degrees Celsius. Stirring and heating continued at 75 degrees Celsius for a total reaction time of about 7 hours.

To 20 grams of the binder polymer solution at 16.2 percent polymer in ethanol, was added 3.24 grams of polyacrylate superabsorbent designated FAVOR 9543, manufactured by Stockhausen, Inc., Greensboro, N.C. The particle size was segregated by sieving and utilizing the fraction that passed through a 600 micron screen and was retained on a 300 micron screen. This mixture provided a 1:1 ratio of binder polymer to polyacrylate superabsorbent. The mixture was poured into a polystyrene weighing dish and dried for 16 hours at room temperature to provide a flexible film with embedded superabsorbent particles.

A portion of the dry SAP/binder film, weighing 0.56 grams, was sealed in a tea bag and immersed in 0.9% saline for 60 minutes. The tea bag containing the swollen film was centrifuged for 3 minutes at 1600 rpm (equivalent to 3 Gs) to remove free fluid. The polymer film had absorbency of 13.6 grams of 0.9 percent saline per gram of dry SAP/binder film. A sample of the FAVOR 9543 polyacrylate superabsorbent tested under the same conditions had absorbency of 22.7 grams of 0.9 percent saline per gram of dry SAP. Since the binder polymer had absorbency of 6.8 g/g, the theoretical absorbency for this film composition is: 0.5×6.8 g/g+0.5× 22.7 g/g=14.7 g/g. The observed absorbency, 13.6 g/g was 92% of the theoretical absorbency. Therefore, the encapsulation of the SAP into the binder film has a minimal impact on the absorbency of the non-encapsulated combination of SAP and binder film.

Example 7

A portion of the polymer solution from Example 6 was treated with sodium hydroxide solution to neutralize a portion (50%) of acrylic acid units in the binder polymer in order to increase the absorbency of the crosslinked film generated by drying the solution. The neutralization was done by adding 5.25 grams of a 48.5% sodium hydroxide solution to 236 grams of polymer solution (16.2% polymer) and stirring at room temperature for 5 minutes.

To 20 grams of this binder polymer solution at 15.0 percent polymer in ethanol/water, was added 3.0 grams of polyacrylate superabsorbent designated FAVOR 9543, manufactured at Stockhausen, Inc., Greensboro, N.C. The particle size was segregated by sieving and utilizing the fraction that passed through a 600 micron screen and was retained on a 300 micron screen. This mixture provided a 1:1 ratio of binder polymer to polyacrylate superabsorbent. The mixture was poured into a polystyrene weighing dish and dried for 16 hours at room temperature to provide a flexible film with embedded superabsorbent particles.

A portion of the dry SAP/binder film, weighing 0.73 grams, was sealed in a tea bag and immersed in 0.9% saline for 60 minutes. The tea bag containing the swollen film was centrifuged for 3 minutes at 1600 rpm (equivalent to 3 Gs) to remove free fluid. The polymer film had absorbency of 14.0 grams of 0.9 percent saline per gram of dry SAP/binder film. A sample of the FAVOR 9543 polyacrylate superabsorbent tested under the same conditions had absorbency of 22.7 grams of 0.9 percent saline per gram of dry SAP. The absorbency of the binder film was measured separately from the particles using the same test method. The binder film had absorbency of 6.8 g/g. Since the binder polymer had absorbency of 6.8 g/g the theoretical absorbency for this film composition is: 0.5×6.5 g/g+0.5×22.7 g/g=14.5 g/g. The observed absorbency, 13.6 g/g was 97% of the theoretical absorbency. Therefore the encapsulation of the SAP into the binder film has a minimal impact on the absorbency of the non-encapsulated combination of SAP and binder film.

Example 8

A binder polymer was prepared as described in Example 6, except that the ratio of monomers was changed to acrylic acid (36 mass %), poly(ethylene glycol) methyl ether methacrylate (62 mass %) and 3-(trimethoxysilyl)propyl methacrylate (2 mass %). Sodium hydroxide solution was used to neutralize a portion (70%) of acrylic acid units in the binder polymer. Additional water was added to reduce the solution viscosity. The solvent composition was approximately 83% ethanol and 17% water with a binder polymer content of ten percent by weight.

Detergent powder (ALL Detergent made by Lever Brothers Company, Greenwich, Conn., or SPARKLEEN Laboratory Detergent, distributed by Fisher Scientific Co.) was distributed evenly onto the surface of a sample of surge material made according to U.S. Pat. No. 5,364,382, manufactured by Kimberly-Clark. The basis weight of the surge sample was 100 gsm. This sample was then sprayed with the binder in a lab-scale spray unit designed to apply a uniform and consistent amount of the binder solution onto the substrate. The lab-scale spray unit is designed to closely resemble the operation of a commercial airlaid machine using emulsion binder as a sole means of stabilization of an airlaid composite. The equipment is housed in a small-framed housing and placed in a laboratory hood. The unit has a stationary sample holder (10×13 inches) in the center of the unit and a moveable spray header directly over the sample holder. A vacuum box is installed under the sample holder section to draw the spray into the substrate. The substrate to be treated is placed on the vacuum box. The binder to be applied to the substrate is housed in a pressurized storage vessel located outside the spray cabinet and is capable of withstanding up to 1000 psig of pressure. The binder is delivered to the spray nozzles via high pressure flexible tubing. The spray header, with nozzles from Spraying Systems Co., is moved over the substrate by means of a belt-driven slide assembly to provide the desired application uniformity and speed. The spray header was operated at a speed of 80 feet per minute at a spray atomization pressure of 100 psig. After spray application the substrate was manually moved to a Mathis through-air-dryer oven, available from Werner Mathis in Palmer, Pa., and dried for 3 minutes at 150 degrees Celsius.

The spray unit was fabricated at Kimberly-Clark Corporation, located in Neenah, Wis. The cabinet housing the unit and the spray header was fabricated by the Airline Hydraulics Corporation located in Bethlehem, Pa. The spray nozzle (UNIJET—TP-8001E-SS) was obtained from Spraying Systems Company located in Wheaton, Ill. The stainless steel pressurized storage vessel (1000 ml capacity) and other fittings for spray chemicals were obtained from Swagelok-Whitey Corporation located in Appleton, Wis. The vacuum for the unit was supplied to the unit by a six gallon wet/dry vacuum cleaner (Model 3 UP77) obtained from Grainger Catalog.

20% binder (by weight) was sprayed onto the surge sample to adhere the detergent powder to the substrate. The amounts of detergent and binder added are shown in Table 8.

TABLE 8

Amount of Detergent Powder Attached to Surge Substrate

| Sample | Detergent | Final Basis Weight (gsm) | Binder Basis Weight (gsm) | Detergent Basis Weight (gsm) |
|---|---|---|---|---|
| 1a | ALL Detergent | 887 | 157 | 630 |
| 2a | ALL Detergent | 825 | 145 | 580 |
| 3a | ALL Detergent | 996 | 179 | 717 |
| 1b | SPARKLEEN | 889 | 158 | 631 |
| 2b | SPARKLEEN | 895 | 159 | 636 |
| 3b | SPARKLEEN | 947 | 169 | 678 |

The binder polymer provided secure attachment of the detergent to the surge substrate and ready-release of the detergent when the substrate is wetted. This material, containing a predetermined amount of laundry detergent or cleaning powder, provides a convenient dispensing form for household laundry use or as a small package for use in a car, boat, or recreational vehicle.

Example 9

TABLE 9

Integrity and Absorbency

| Sample | Sample Description | Tensile Strength (g/gsm) | CRC (g/g) | Basis Weight (gsm) |
|---|---|---|---|---|
| A | 50% 9543 SAP/47% CR1654 pulp/ 3% T255 | 1.0 | 11.0 | 668 |
| B | 50% 9543 SAP/45% CR1654 pulp/ 5% T255 | 2.4 | 9.9 | 695 |
| C | 50% 9543 SAP/43% CR1654 pulp/ 7% T255 | 3.7 | 11.4 | 728 |
| D | 50% 9543 SAP/40% CR1654 pulp/ 10% T255 | 5.8 | 9.7 | 749 |
| E | 50% 9543 SAP/46% NB416 pulp/ 4% T255 | 6.1 | 10.7 | 742 |
| F | 50% 9543 SAP/50% PXL pulp | 0.2 | 10.2 | 601 |
| G | 45% 9543 SAP/45% CF416 pulp/ 10% crosslinkable binder composition | 8.1 | 9.1 | 814 |
| H | 52.5% 9543 SAP/42.5% CF416 pulp/ 15% crosslinkable binder composition | 8.7 | 8.1 | 874 |
| I | 75% 9543 SAP/25% crosslinkable binder composition on 17 gsm spunbond | 11.8 | 14.9 | 378 |
| J | 75% 9543 SAP/25% crosslinkable binder composition on 100 gsm UCTAD | 14.2 | 10.1 | 571 |

Samples A–E, G, and H in Example 9 were hand-made using a handsheet former. Superabsorbent FAVOR 9543, produced by Stockhausen, and fibers were uniformly mixed by air circulation in the former. The samples were heated at 150 degrees Celsius for 5 minutes, densified to 0.2 g/cc to activate binding of the T255 (polyethylene/polypropylene bicomponent binder fiber available from KOSA, located in Salisbury, N.C.). CR1654 pulp is available from U.S. Alliance Forest Products located in Coosa River, Ala. CF416 and NB416 are Southern pine kraft fibers available from Weyerhaeuser Inc. in Columbus, Miss., and Newburn, N.C., respectively.

Samples G and H were prepared in the handsheet former at an approximate basis weight of 365 gsm and sprayed with binder solution 3b, prepared as described in Example 3. The spray unit is described in Example 8. After spray application of the binder two sheets were laminated together and then dried for 3 minutes at 150 degrees Celsius.

Sample I was made with a binder composition prepared as described in Example 8 which was subsequently neutralized to 70% of the acrylic acid units with sodium hydroxide solution. 40 grams of this solution, at 10% polymer concentration, was mixed with 16 grams of FAVOR 9543, available from Stockhausen Inc., located in Greensboro, S.C. The SAP/binder mixture was spread onto 17 gsm polypropylene spunbond nonwoven fabric treated for wettability with AHCOVEL N-62 surfactant. This spunbond material is available from Kimberly-Clark, located in Dallas, Tex. The coated spunbond was allowed to dry for 18 hours at room temperature in a laboratory hood.

Test Method for Determining Absorbency Under Zero Load (AUZL)

The Absorbency Under Zero Load (AUZL) is a test which measures the ability of an absorbent material to absorb a liquid (such as a 0.9 weight percent solution of sodium chloride in distilled water) while under a negligible load or restraining force. About 0.16 g of particulate SAP are weighed and placed into a plastic sample cup. The sample cup includes a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder. The sample is then covered with a plastic spacer disc, weighing 4.4 grams, which generates a pressure of about 0.01 pound per square inch. The sample cup is placed in a Petri dish which contains about 25 ml of 0.9% by weight sodium chloride solution. After one hour, the cup is taken out and placed on multiple layers of paper towels to blot the interstitial fluid of the web or coform. The blotting is continued by moving the cup to the area with dry paper towel until there is no fluid mark visible on the paper towel. The weight difference of the cup between wet and dry presents total amount of fluid absorbed by the web or coform and is used to calculate AUZL.

Test Method for Determining Absorbency Under Load for Composites (AULC)

The Absorbency Under Load for Composites (AULC) is a test which measures the ability of an absorbent material to absorb a liquid (such as a 0.9 weight percent aqueous solution of sodium chloride) while under an applied load or restraining force. The AULC method provides a slight positive head of fluid for the absorbent material, which is allowed to swell under a restraining load. The material is drained under vacuum at the end of the test.

The AULC test cup is cylindrical with a height of at least 1.75 inches; the inner diameter describes a cylinder, the base of which has an area of 4.37 in$^2$. The bottom of the test cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder. A spacer weighing about 60 grams and having a circular diameter of about 2.36 inches is made to fit within the AULC test cup without binding. The spacer is formed with multiple cylinder holes of about 9 mm diameter, providing an open area of about 52%. A 100 mesh screen is adhered to the bottom of the spacer in a similar manner as the mesh which is attached to the bottom of the test cup or other suitable method. Weights are sized to fit on top of the spacer. The first weight should apply a load of 600 grams (in combination with the spacer), and the second weight, in combination with the first weight and the spacer disc, should apply a load of 1800 grams.

Additional equipment required includes a vacuum trap for liquid that is suctioned out of the composite material at the end of the test, shallow dishes such as Petri dishes or plastic weighing boats suitable for holding an excess amount of liquid than will be imbibed by the sample, and a thin mesh screen with a thickness between 0.3 mm and 0.75 mm and a mesh size of about 1.2 mm. The vacuum trap is adapted to apply vacuum to an area matching the dimensions of the bottom of the AULC testing cup (for example, a larger vacuum area may be selectively screened with a relatively impermeable material except in an area matching the dimensions of the bottom of the AULC cup). The vacuum applied is about 27 inches of mercury.

Composite samples are cut to fit inside the AULC testing cup. Airlaid or nonwoven-based materials are cut into circles 2.35 inches in diameter. Airformed samples are cut or formed into circles, each with a diameter of 2.312 inches.

To carry out the test, test cup and spacer should be clean and dry. The test cup and spacer to be used in each trial should be weighed together (Measurement 1), and the mass recorded. The specimen is placed in the sample cup and the spacer is placed on top of the sample in the cup. The assembly is then weighed (Measurement 2), and the mass is recorded. The appropriate amount of weight is placed atop the spacer, if required. The spacer alone applies a force of 0.03 pounds per square inch of area (psia; the disc and first weight, with a net mass of 600 grams, apply a force of 0.3 psi, and the disc and both weights together, having a net mass of 1800 grams, apply a force of 0.9 psi).

The cup holding the specimen is placed in a pool of excess fluid in the shallow dish on top of the mesh screen and a one hour timer is started immediately. The level of fluid in the dish is maintained between about 1 mm and 2 mm depth. Following one hour, the specimen is removed from the fluid bath. Any fluid that may have accumulated atop the specimen should be poured off without displacing any weights atop the spacer disc. The specimen assembly is then placed on the vacuum box, with any weights still in place. Vacuum is applied to the sample for 30 seconds.

Any weights atop the spacer are then removed from the assembly and the assembly is weighed again (Measurement 3). The mass is recorded.

The dry weight of the specimen is calculated by subtracting Measurement 1 from Measurement 2. The amount of fluid absorbed by the specimen is calculated by subtracting Measurement 2 from Measurement 3. The absorbency under load of the composite material is calculated as the amount of fluid absorbed divided by the dry weight of the specimen.

At least three specimens of each sample should be measured, and the absorbency under load values should be averaged to obtain an overall absorbency under load for the composite sample.

Test Method for Determining Stiffness

A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester, Model 4171-E, manufactured by Teledyne Gurley, a business having offices in Troy, N.Y. For purposes of the present invention, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

Test Method for Determining Absorbent Capacity

Centrifuge Retention Capacity: The Centrifuge Retention Capacity (CRC) is a test which measures the amount in grams of a test liquid, such as water or a 0.9 weight percent solution of sodium chloride in distilled water, that a gram of a material can absorb or immobilize in a single time interval, or a series of time intervals, after being subjected to a centrifugal force for a period of time.

Stock teabag material is cut into a 3-inch (about 7.6 centimeters) by 5-inch (about 12.7 centimeters) rectangle and folded in half to form a 2.5-inch (about 6.4 centimeters)

by 3-inch (about 7.6 centimeters) rectangle with the sealable face inward. Two of the three open sides are heat sealed with the inside edge of the seal about 0.25 inch (about 0.64 centimeter) from the edge. About 0.2 gram of sample material (or a 1-inch by 1-inch square piece of composite) is placed into a preweighed teabag, and the open end of the teabag is heat sealed. The teabag is submerged in a pan of test liquid for a time interval, removed, allowed to drain on a wire mesh at about a 45 degree angle for about 2 minutes, centrifuged for about 3 minutes at 290 times the gravitational force and then weighed. If a series of time intervals is to be run, the sample is returned to the test liquid until the next time interval. After each time interval, the teabag is again allowed to drain on the wire mesh for about 2 minutes, again centrifuged for about 3 minutes at 290 times the gravitational force, and then weighed again. After the final time interval, the teabag is then allowed to dry and then weighed again. A blank test is also run by centrifuging under similar conditions an empty teabag which had also been placed in the test liquid. The weight of the test liquid retained per gram of dry sample material after centrifuging is calculated from the data obtained, and this is expressed as the Centrifuge Retention Capacity value in terms of grams of test liquid retained per gram of dry sample material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A fluid storage material, comprising:
 a plurality of particles secured to one another with an absorbent crosslinkable binder composition, the binder composition including a polymer having a silane functional group.

2. The fluid storage material of claim 1, wherein the particles comprise superabsorbent particles.

3. The fluid storage material of claim 1, wherein the particles comprise an encapsulated agent.

4. The fluid storage material of claim 3, wherein the agent is selected from a group consisting of fragrance agents, cleansing agents, and skin rejuvenation agents.

5. The fluid storage material of claim 1, wherein the particles comprise a powder.

6. The fluid storage material of claim 5, wherein the powder comprises at least one of a group consisting of activated carbon and sodium bicarbonate.

7. The fluid storage material of claim 1, further comprising a plurality of fibers secured to the particles with the absorbent crosslinkable binder composition.

8. The fluid storage material of claim 7, wherein the fibers comprise at least one of a group consisting of northern hardwood fibers, southern hardwood fibers, mercerized southern hardwood fibers, softwood fibers, chemically stiffened southern softwood pulps, cross-linked pulps, cellulose powders, superabsorbent fibers, regenerated cellulose fibers, cotton, cellulose acetate, non-cellulosic fibers, polyester fibers, acrylic fibers, polyethylene fibers, polypropylene fibers, polyamide fibers, polylactide fibers, and combinations thereof.

9. The fluid storage material of claim 1, wherein the absorbent crosslinkable binder composition comprises a crosslinkable binder that is sufficiently hydrophilic to provide uninhibited access of aqueous fluids to the particles.

10. The fluid storage material of claim 1, wherein the absorbent crosslinkable binder composition comprises a soluble binder selected from a group consisting of hydrophilic polymers, a blend of hydrophilic polymers containing hydrophilic agents, and a blend of hydrophobic polymers containing hydrophilic agents.

11. The fluid storage material of claim 1, wherein the absorbent crosslinkable binder composition comprises an alkoxysilane grafted poly(ethylene oxide).

12. The fluid storage material of claim 11, wherein the alkoxysilane comprises methacryloxypropyl trimethoxy silane.

13. The fluid storage material of claim 1, wherein the absorbent crosslinkable binder composition comprises a binder having a glass transition temperature below 10 degrees Celsius.

14. The fluid storage material of claim 1, wherein the absorbent crosslinkable binder composition comprises acrylic acid copolymers.

15. The fluid storage material of claim 14, wherein the acrylic acid copolymers comprise acrylic acid and long chain, hydrophilic acrylate esters.

16. The fluid storage material of claim 14, wherein the acrylic acid copolymers comprise acrylic acid and long chain, hydrophilic methacrylate esters.

17. The fluid storage material of claim 14, wherein the acrylic acid copolymers comprise acrylic acid salts and long chain, hydrophilic methacrylate esters.

18. The fluid storage material of claim 14, wherein the acrylic acid copolymers comprise acrylic acid and poly(ethylene glycol) methacrylate having from 1 to 13 ethylene glycol units.

19. The fluid storage material of claim 14, wherein the acrylic acid copolymers comprise acrylic acid salts and poly(ethylene glycol) methacrylate having from 1 to 13 ethylene glycol units.

20. The fluid storage material of claim 14, wherein the acrylic acid copolymers comprise an ester having a functional group that is capable, upon exposure to water, to form a silanol functional group which condenses to form a crosslinked polymer.

21. The fluid storage material of claim 1, wherein the absorbent crosslinkable binder composition further comprises a modifying agent selected from a group consisting of plasticizers, colorants, stabilizers, flow aids, and preservatives.

22. The fluid storage material of claim 1, wherein the absorbent crosslinkable binder composition has an absorbent capacity of at least 5 grams per gram.

23. The fluid storage material of claim 1, wherein the absorbent crosslinkable binder composition has an absorbent capacity of at least 10 grams per gram.

24. The fluid storage material of claim 1, wherein the fluid storage material has a density of at least 0.5 g/cm$^3$.

25. The fluid storage material of claim 1, wherein the fluid storage material has a density of at least 0.7 g/cm$^3$.

26. The fluid storage material of claim 1, wherein the fluid storage material has a Gurley stiffness value of less than 320 mg.

27. The fluid storage material of claim 1, wherein the fluid storage material has a Gurley stiffness value of less than 160 mg.

28. A personal care product, comprising the fluid storage material of claim 1.

29. The personal care product of claim 28, wherein the fluid storage material has a thickness of between about 0.2 and about 4 millimeters.

30. A fluid storage material, comprising:
a substrate; and
particles secured to the substrate with an absorbent crosslinkable binder composition, the binder composition including a polymer having a silane functional group.

31. The fluid storage material of claim 30, wherein the particles comprise superabsorbent particles.

32. The fluid storage material of claim 30, wherein the particles comprise an encapsulated agent.

33. The fluid storage material of claim 32, wherein the agent is selected from a group consisting of fragrance agents, cleansing agents, and skin rejuvenation agents.

34. The fluid storage material of claim 30, wherein the particles comprise a powder.

35. The fluid storage material of claim 34, wherein the powder comprises at least one of a group consisting of activated carbon and sodium bicarbonate.

36. The fluid storage material of claim 30, further comprising a plurality of fibers secured to the substrate with the absorbent crosslinkable binder composition.

37. The fluid storage material of claim 36, wherein the fibers comprise at least one of a group consisting of northern hardwood fibers, southern hardwood fibers, mercerized southern hardwood fibers, softwood fibers, chemically stiffened southern softwood pulps, cross-linked pulps, cellulose powders, superabsorbent fibers, regenerated cellulose fibers, cotton, cellulose acetate, non-cellulosic fibers, polyester fibers, acrylic fibers, polyethylene fibers, polypropylene fibers, polyamide fibers, polylactide fibers, and combinations thereof.

38. The fluid storage material of claim 30, wherein the absorbent crosslinkable binder composition comprises a crosslinkable binder that is sufficiently hydrophilic to provide uninhibited access of aqueous fluids to the particles.

39. The fluid storage material of claim 30, wherein the absorbent crosslinkable binder composition comprises a latent crosslinker including multivalent metal ions.

40. The fluid storage material of claim 30, wherein the absorbent crosslinkable binder composition comprises a soluble binder selected from a group consisting of hydrophilic polymers, a blend of hydrophilic polymers containing hydrophilic agents, and a blend of hydrophobic polymers containing hydrophilic agents.

41. The fluid storage material of claim 30, wherein the absorbent crosslinkable binder composition comprises an alkoxysilane grafted poly(ethylene oxide).

42. The fluid storage material of claim 41, wherein the alkoxysilane comprises methacryloxypropyl trimethoxy silane.

43. The fluid storage material of claim 30, wherein the absorbent crosslinkable binder composition comprises a binder having a glass transition temperature below 30 degrees Celsius.

44. The fluid storage material of claim 30, wherein the absorbent crosslinkable binder composition comprises a binder having a glass transition temperature below 10 degrees Celsius.

45. The fluid storage material of claim 30, wherein the absorbent crosslinkable binder composition comprises acrylic acid copolymers.

46. The fluid storage material of claim 45, wherein the acrylic acid copolymers comprise acrylic acid and long chain, hydrophilic acrylate esters.

47. The fluid storage material of claim 45, wherein the acrylic acid copolymers comprise acrylic acid and long chain, hydrophilic methacrylate esters.

48. The fluid storage material of claim 45, wherein the acrylic acid copolymers comprise acrylic acid salts and long chain, hydrophilic methacrylate esters.

49. The fluid storage material of claim 45, wherein the acrylic acid copolymers comprise acrylic acid and poly (ethylene glycol) methacrylate having from 1 to 13 ethylene glycol units.

50. The fluid storage material of claim 45, wherein the acrylic acid copolymers comprise acrylic acid salts and poly(ethylene glycol) methacrylate having from 1 to 13 ethylene glycol units.

51. The fluid storage material of claim 45, wherein the acrylic acid copolymers comprise an ester having a functional group that is capable, upon exposure to water, to form a silanol functional group which condenses to form a crosslinked polymer.

52. The fluid storage material of claim 30, wherein the absorbent crosslinkable binder composition further comprises a modifying agent selected from a group consisting of plasticizers, colorants, stabilizers, flow aids, and preservatives.

53. The fluid storage material of claim 30, wherein at least 20% of the particles remain secured to the substrate following immersion of the fluid storage material in 0.9% saline solution for at least 30 minutes.

54. The fluid storage material of claim 30, wherein at least 30% of the particles remain secured to the substrate following immersion of the fluid storage material in 0.9% saline solution for at least 30 minutes.

55. The fluid storage material of claim 30, wherein the fluid storage material has an absorbent capacity of at least 0.2 grams per square centimeter under an applied load of 0.3 psi.

56. The fluid storage material of claim 30, wherein the fluid storage material has an absorbent capacity of at least 0.6 grams per square centimeter under an applied load of 0.3 psi.

57. The fluid storage material of claim 30, wherein the fluid storage material has a density of at least 0.1 g/cm$^3$.

58. The fluid storage material of claim 30, wherein the fluid storage material has a density of at least 0.4 g/cm$^3$.

59. The fluid storage material of claim 30, wherein the fluid storage material has a Gurley stiffness value of less than 400 mg.

60. The fluid storage material of claim 30, wherein the fluid storage material has a Gurley stiffness value of less than 200 mg.

61. The fluid storage material of claim 30, wherein the substrate is selected from a group consisting of nonwoven webs, woven webs, knitted fabrics, cellulosic tissue sheets, plastic films, foams, stranded composites, and elastomer net composites.

62. The fluid storage material of claim 30, wherein the substrate comprises a plastic film including at least one of a group consisting of polypropylene, low density polyethylene, high density polyethylene, linear low density polyethylene, ultra low density polyethylene, styrene-ethylene-butylene-styrene block copolymers, styrene-isoprene-styrene block copolymers, metallocene catalyzed elastomers, metallocene catalyzed plastomers, monolithic breathable films, polyether amide based polymers, and ether/ester polyurethane thermal-plastic elastomers.

63. A personal care product, comprising the fluid storage material of claim 30.

64. The personal care product of claim 63, wherein the substrate is non-absorbent.

65. The personal care product of claim 63, wherein the fluid storage material has a thickness of between about 0.2 and about 4 millimeters.

66. The personal care product of claim 63, wherein the fluid storage material has an absorbent capacity of between about 0.1 and about 1.8 grams per square centimeter under an applied load of 0.3 psi.

67. A training pant comprising the personal care product of claim 63.

68. A feminine hygiene product comprising the personal care product of claim 63.

* * * * *